(12) United States Patent
Arghavani et al.

(10) Patent No.: US 6,245,928 B1
(45) Date of Patent: *Jun. 12, 2001

(54) WATER SOLUBLE TRI-SUBSTITUTED 1,2-DIOXETANE COMPOUNDS HAVING INCREASED STORAGE STABILITY, SYNTHETIC PROCESSES AND INTERMEDIATES

(75) Inventors: Zahra Arghavani, Southfield; Hashem Akhavan-Tafti, Brighton; Renuka DeSilva, Northville; Kumar Thakur, Southfield, all of MI (US)

(73) Assignee: Lumigen, Inc., Southfield, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,263

(22) Filed: Feb. 17, 2000

Related U.S. Application Data

(63) Continuation of application No. 09/101,331, filed as application No. PCT/US97/19618 on Nov. 7, 1997, now Pat. No. 6,036,892, which is a continuation-in-part of application No. 08/748,107, filed on Nov. 8, 1996, now Pat. No. 5,721,370, which is a continuation-in-part of application No. 08/509,305, filed on Jul. 31, 1995, now Pat. No. 5,577,135.

(51) Int. Cl.[7] ........................................................ C07F 9/06
(52) U.S. Cl. ............................ 558/167; 558/179; 558/182; 558/169; 562/8; 562/25
(58) Field of Search ........................................ 558/167, 168, 558/169, 179, 182; 562/8, 24, 25

(56) References Cited

U.S. PATENT DOCUMENTS

| | | | |
|---|---|---|---|
| 5,777,135 | * | 7/1998 | Arghavani et al. .................. 252/700 |
| 6,036,892 | * | 3/2000 | Arghavani et al. .................. 549/332 |

* cited by examiner

*Primary Examiner*—Jean F. Vollano
(74) *Attorney, Agent, or Firm*—Richard S. Handley

(57) ABSTRACT

Stable, enzymatically triggered chemiluminescent 1,2-dioxetanes with improved water solubility and storage stability are provided as well as synthetic processes and intermediates used in their preparation. Dioxetanes further substituted with two or more water-solubilizing groups disposed on the dioxetane structure and an additional fluorine atom or lower alkyl group provide superior performance by eliminating the problem of reagent carryover when used in assays performed on capsule chemistry analytical systems. These dioxetanes display substantially improved stability on storage. Compositions comprising these dioxetanes, a non-polymeric cationic surfactant enhancer and optionally a fluorescer, for providing enhanced chemiluminescence are also provided.

11 Claims, 5 Drawing Sheets

WATER SOLUBLE TRI-SUBSTITUTED 1,2-DIOXETANE COMPOUNDS HAVING INCREASED STORAGE STABILITY, SYNTHETIC PROCESSES AND INTERMEDIATES

CROSS REFERENCE TO RELATED APPLICATIONS

This application is a continuing application of applicants' U.S. application Ser. No. 09/101,331 filed on Jul. 7, 1998, now U.S. Pat. No. 6,036,892, as the result of national stage entry from PCT Application US97/19618 filed Nov. 7, 1997 which is a continuation-in-part of applicants' U.S. application Ser. No. 08/748,107 filed on Nov. 8, 1996, now U.S. Pat. No. 5,721,370, which is a continuation-in-part of applicants' U.S. application Ser. No. 08/509,305 filed on Jul. 31, 1995, now U.S. Pat. No. 5,577,135.

BACKGROUND OF THE INVENTION (1) Field of the Invention

The present invention relates generally to stable 1,2-dioxetanes and compositions which can be triggered by chemical reagents, including enzymes, to generate chemiluminescence. The dioxetanes contain more than one ionizable group which are part of an alkoxy substituent. The dioxetanes further contain a fluorine atom or lower alkyl group substituted for one of the hydrogen atoms on the alkoxy substituent which improve the storage stability of the dioxetane. The present invention, in particular, further relates to methods of synthesis of such dioxetanes.

The dioxetanes which are prepared by the synthetic processes of the present invention are useful in compositions containing the dioxetane, a cationic surfactant and optionally a fluorescer which enhance the amount of chemiluminescence which is produced. Dioxetanes and enhanced compositions of the present invention are useful in methods for generating light (chemiluminescence) and in methods of analysis for detecting the presence or amount of an analyte. Importantly, the ionizable groups afford a more water soluble dioxetane and solve an unexpected chemical carry-over problem in capsule chemistry analytical systems, while the presence of the fluorine atom or lower alkyl group improves the storage stability of the dioxetane.

(2) Description of Related Art a. Enzymatically Triggerable Dioxetanes. The first examples of enzymatic triggering of dioxetanes are described in a U.S. patent application (A. P. Schaap, U.S. patent application Ser. No. 887,139) and a series of papers (A. P. Schaap, R. S. Handley, and B. P. Giri, *Tetrahedron Lett.*, 935 (1987); A. P. Schaap, M. D. Sandison, and R. S. Handley, *Tetrahedron Lett.*, 1159 (1987) and A. P. Schaap, *Photochem. Photobiol.*, 47S, 50S (1988)). The highly stable adamantyl-substituted dioxetanes bearing a protected aryloxide substituent are triggered to decompose with emission of light by the action of both an enzyme and aqueous buffer to give a strongly electron-donating aryloxide anion which dramatically increases the rate of decomposition of the dioxetane. As a result, chemiluminescence is emitted at intensities several orders of magnitude above that resulting from slow thermal decomposition of the protected form of the dioxetane. U.S. Pat. No. 5,068,339 to Schaap discloses enzymatically triggerable dioxetanes with covalently linked fluorescer groups decomposition of which results in enhanced chemiluminescence via energy transfer to the fluorescer. U.S. Pat. Nos. 5,112,960 and 5,220,005 and a PCT application (WO88/00695) to Bronstein disclose triggerable dioxetanes bearing substituted adamantyl groups. U.S. Pat. No. 4,952,707 to Edwards discloses phosphate-substituted dioxetanes. A PCT application (WO94/26726) to Bronstein discloses adamantyl dioxetanes bearing a phenyl or naphthyl group substituted at a non-conjugated position with an enzyme labile OX group and with an additional group on the aryl ring.

Other triggerable dioxetanes are disclosed in a PCT application (WO94/10258) to Wang. The dioxetanes disclosed in Wang contain an alkoxy group which may be mono-substituted and a substituted phenyl-OX group wherein one or more non-hydrogen groups are present on the benzene ring substituent in addition to the triggerable OX group.

Dioxetanes disclosed in all of the foregoing publications generate a light-emitting carbonyl compound comprising an alkyl ester of an aromatic carboxylic acid, typically the methyl ester of a hydroxybenzoic or hydroxynaphthoic acid or else a hydroxyaryl ketone.

Applicants' co-pending U.S. application Ser. No. 08/509,305 ('305 application) filed on Jul. 31, 1995 discloses disubstituted dioxetanes whose hydroxy dioxetane shows improved water solubility and is fully incorporated herein by reference.

b. Surfactant Enhancement of Chemiluminescence from Triggerable Dioxetanes. Enhancement of chemiluminescence from the enzyme-triggered decomposition of a stable 1,2-dioxetane in the presence of water-soluble substances including an ammonium surfactant and a fluorescer has been reported (A. P. Schaap, H. Akhavan and L. J. Romano, Clin. Chem., 35(9), 1863 (1989)). Fluorescent micelles consisting of cetyltrimethylammonium bromide (CTAB) and 5-(N-tetradecanoyl)amino-fluorescein capture the intermediate hydroxy-substituted dioxetane and lead to a 400-fold increase in the chemiluminescence quantum yield by virtue of an efficient transfer of energy from the anionic form of the excited state ester to the fluorescein compound within the hydrophobic environment of the micelle.

U. S. Pat. Nos. 4,959,182 and 5,004,565 to Schaap describe additional examples of enhancement of chemiluminescence from chemical and enzymatic triggering of stable dioxetanes in the presence of micelles formed by the quaternary ammonium surfactant CTAB. Fluorescent micelles also enhance light emission from the base-triggered decomposition of hydroxy- and acetoxy-substituted dioxetanes.

U.S. Pat. No. 5,145,772 to Voyta discloses enhancement of enzymatically generated chemiluminescence from 1,2-dioxetanes in the presence of polymers with pendant quaternary ammonium groups alone or admixed with fluorescein. Other substances reported to enhance chemiluminescence include globular proteins such as bovine albumin and quaternary ammonium surfactants. Other cationic polymer compounds were marginally effective as chemiluminescence enhancers; nonionic polymeric compounds were generally ineffective and an anionic polymer significantly decreased light emission. A PCT application (WO 94/21821) to Bronstein describes the use of mixtures of the aforementioned polymeric quaternary ammonium surfactant enhancers with enhancement additives.

The enhancement and catalysis of a non-triggerable dioxetane by pyranine in the presence of CTAB is described (Martin Josso, Ph.D. Thesis,Wayne State University (1992), Diss. Abs. Int., Vol. 53, No. 12B, p. 6305).

U.S. Pat. No. 5,393,469 to Akhavan-Tafti discloses enhancement of enzymatically generated chemiluminescence from 1,2-dioxetanes in the presence of polymeric quaternary phosphonium salts optionally substituted with fluorescent energy acceptors.

European Patent Application Serial No. 94108100.2 discloses enhancement of enzymatically generated chemiluminescence from 1,2-dioxetanes in the presence of dicationic phosphonium salts. No documents disclose the combination of an anionic fluorescer and a dicationic enhancer for enhancing chemiluminescence from a triggerable dioxetane. No example of enhancement of substituted dioxetanes of the type of the present invention has been reported.

c. Triggerable Dioxetanes with Improved Water Solubility. The enzymatically triggerable dioxetanes are now undergoing widespread use as substrates for marker enzymes in numerous applications including immunoassays, gene expression studies, Western blotting, Southern blotting, DNA sequencing and the identification of nucleic acid segments in infectious agents. Despite the growing use of these compounds, there are limitations to there use in some assay methods. Triggerable dioxetanes whose hydroxy dioxetane deprotected form are more water-soluble are desirable. As shown in the structures below, it is especially desirable that the hydroxy dioxetane formed by the dephosphorylation of a phosphate dioxetane by alkaline phosphatase be highly soluble in aqueous solutions and in compositions containing chemiluminescence enhancing substances. Such dioxetanes and compositions are of importance in certain solution assay methods for detecting hydrolytic enzymes or conjugates of hydrolytic enzymes.

claimed, however, the preparation of such a dioxetane is not described. Significantly, there is no disclosure of what effect the addition of a carboxyl group had, if any, on solubility and other properties of the dioxetane. There is no teaching in the art of how many solubilizing groups are required or what particular advantage might be conferred. Use of solubilizing groups which interfere with the removal of the protecting group which initiates light emission or which otherwise interfere with light production would be of no value. Solubilizing groups which would be removed during the luminescent reaction likewise would not be useful.

In Applicant's co-pending '305 application it was demonstrated that incorporation of one ionic solubilizing group was insufficient to eliminate the carryover problem associated with the hydroxy dioxetane produced by dephosphorylation of a phosphate dioxetane. Phosphate dioxetanes whose hydroxy dioxetane product is highly water soluble and enhanced compositions containing such phosphate dioxetanes were provided to solve this problem. It was subsequently discovered that dioxetanes which provided the solution to the carryover problem, exhibited insufficient storage stability at room temperature. Thus, no dioxetanes known in the art possessed both high solubility of the hydroxy dioxetane and long term storage stability.

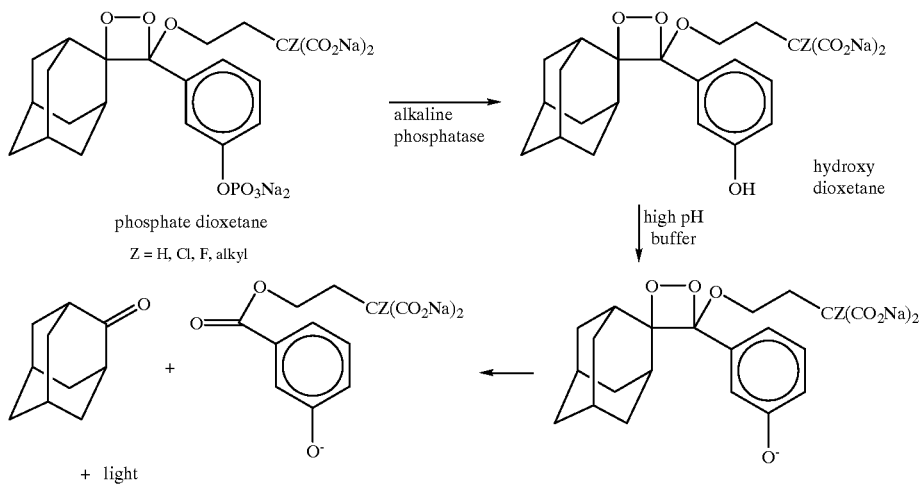

As further background of the present invention and as more fully explained in the examples below, it has been found that use of conventional chemiluminescent dioxetane reagents in assays performed on automated instrumentation based on the principles of capsule chemistry analysis results in carryover of reagent from one fluid segment to another, resulting in potentially inaccurate measurements, erroneous results, and imprecision due to non-reproducibility. Capsule chemistry analysis is described in U.S. Pat. No. 5,399,497, which is fully incorporated by reference herein. It has been postulated that, among other possible means for overcoming the carryover problem, improved water solubility of the hydroxy dioxetane, in particular, might eliminate or minimize carryover of this luminescent reaction intermediate into adjacent fluid segments of a capsule chemistry analysis system.

Dioxetane compounds in commercial use do not incorporate any solubilizing groups which are appended to an alkoxy group. As such, these dioxetanes are unsuitable for use in assay methods requiring zero carryover. A suggestion of incorporating a solubilizing group into a dioxetane has been made (U.S. Pat. No. 5,220,005). A dioxetane with a carboxyl group substituted on an adamantyl substituent is Applicants' 08/748,107 application disclosed that substitution of a hydrogen atom on the alkoxy group bearing two ionic solubilizing groups with a fluorine atom or lower alkyl group dramatically improves the storage stability of these dioxetanes. Synthetic processes for preparing such dioxetanes were disclosed. In the present application, improved processes are disclosed as well as intermediates useful therein.

OBJECTS

It is an object of the present invention to provide enzymatically triggered 1,2-dioxetanes with improved storage stability whose hydroxy dioxetane product formed upon action of a triggering enzyme is highly soluble in aqueous solution. It is a second object of the present invention to provide 1,2-dioxetanes substituted with two or more water-solubilizing ionic groups and either a fluorine atom or lower alkyl group disposed on an alkoxy substituent of the dioxetane structure which provide superior storage stability. It is a further object of the present invention to provide a composition comprising a fluorine or lower alkyl group-substituted dioxetane with two or more ionic water-solubilizing groups, a non-polymeric cationic enhancer and optionally a fluorescer, for providing enhanced chemiluminescence. It is a further object of the present invention to provide dioxetanes and compositions which, when used in assays performed on capsule chemistry analytical systems, eliminate the problem of reagent carryover and have extended storage stability. It is yet another object of the present invention to provide a synthetic process and intermediates useful therein for the preparation of 1,2-dioxetanes substituted with two or more water-solubilizing ionic groups and either a fluorine atom or lower alkyl-group disposed on an alkoxy substituent of the dioxetane structure.

DESCRIPTION OF THE PREFERRED EMBODIMENTS

Figure 1:
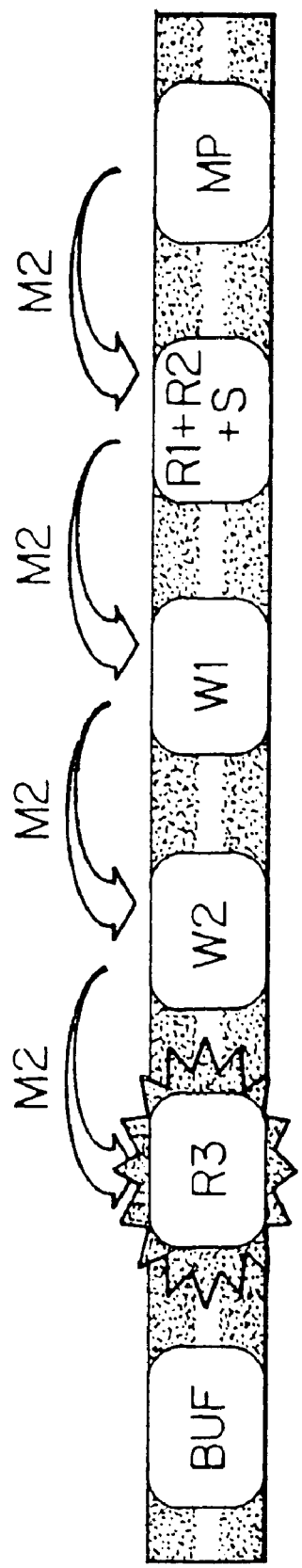
FIG. 1 is a diagram of a capsule chemistry analysis system in which carryover was determined to be a problem.

The present invention relates to dioxetanes with improved storage stability and whose hydroxy dioxetane product formed upon action of a triggering enzyme is highly soluble in aqueous solution and which are triggerable by an enzyme to produce chemiluminescence. Such triggerable dioxetanes eliminate or minimize carryover of the luminescent hydroxy dioxetane into adjacent segments in capsule chemistry analytical systems as described in U.S. Pat. No. 5,399,497. Carryover can result from solubilization, deposition or precipitation of light-emitting material of low water solubility into the fluorocarbon oil which serves as the isolating fluid in capsule chemistry systems. Reagent carryover can lead to inaccurate measurements, erroneous results and imprecision due to irreproducibility.

In the co-pending '305 application it was discovered that dioxetane 1 below was particularly effective for the chemiluminescent detection of alkaline phosphatase in aqueous solution.

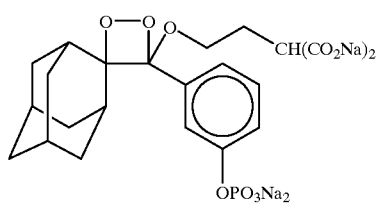

1

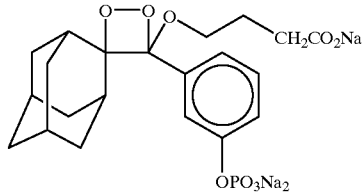

2

For comparison, dioxetane 2 which incorporates only one ionizable group was prepared. This dioxetane did not eliminate the carryover problem discussed above.

Use of dioxetane 1 in the test system described in U.S. Pat. No. 5,399,497 led to complete elimination of the carryover problem. However, it was subsequently discovered unexpectedly, that solutions of dioxetane 1 in aqueous buffer displayed unsatisfactory storage stability. Solutions containing 1 in alkaline buffer displayed significant decomposition after storage at 25° C. for two weeks. Dioxetane 1, in fact, was found to be significantly less stable than a related compound, Lumigen PPD, shown below which has no ionic solubilizing groups on the alkoxy group.

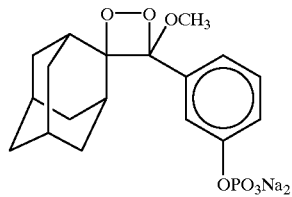

Lumigen PPD

As far as Applicants are aware, there is no teaching in the art of dioxetane chemistry of the cause of the lower stability of 1. Means of structurally modifying 1 to improve its storage stability while preserving its other beneficial properties were disclosed in Applicants' co-pending application Ser. No. 08/748,107 which is fully incorporated herein by reference.

Definitions

Storage stability is related to the rate of decomposition of the dioxetane due to spontaneous reaction and is an intrinsic property. Decomposition of triggerable dioxetanes can also be induced by the presence of trace quantities of agents which catalyze the removal of a protecting group and thus initiate the decomposition. Storage stability of a dioxetane can be assessed by measuring the quantity of dioxetane present in a known sample at periodic intervals. The measurement can take any form known which measures a property relatable to the quantity of dioxetane. Techniques such as spectrophotometry, NMR spectrometry and the like are exemplary. A convenient means is to measure the amount of light produced by reacting a known quantity of dioxetane with a triggering agent under a standard set of conditions. A decrease in the amount or intensity of light emitted signals a loss of dioxetane compound.

Storage stability refers to stability of the dioxetane in both the pure form and as a solution or formulation in a buffer solution. The formulation can also contain various additives for increasing the amount of light produced or for improving the activity of an enzymatic triggering agent. It is desirable that the dioxetane in a formulation not undergo significant decomposition at ambient temperature for a reasonable period of time. Compositions to be used with automated analyzers should desirably be stable for at least 1 week. Upon refrigeration at 0–5° C., it is desirable that no significant decomposition is observed for at least 2–3 months.

More desirably, compositions to be used with automated analyzers should show not more than 2–3% change in the observed indicator of storage stability in about 2–4 weeks.

The solution to the problem of storage stability was found in dioxetanes having the formula I:

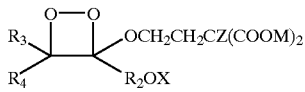

wherein Z is selected from the group consisting of a fluorine atom and an alkyl group of 1–4 carbons and M is selected from hydrogen, an alkali metal ion or a quaternary ammonium or phosphonium ion, wherein $R_3$ and $R_4$ are each selected from acyclic, cyclic and polycyclic organic groups which can optionally be substituted with heteroatoms and which provide stability to the dioxetane, wherein $R_2$ is an aryl ring group selected from phenyl and naphthyl groups which can include additional substituents selected from halogens, alkyl, substituted alkyl, alkoxy, substituted alkoxy, carbonyl, carboxyl, amino and alkylamino groups and wherein X is a protecting group which can be removed by an activating agent to form an oxyanion-substituted dioxetane which decomposes and produces light and two carbonyl-containing compounds, one of which is an oxyanion-substituted ester compound containing two carboxylate groups, as shown below.

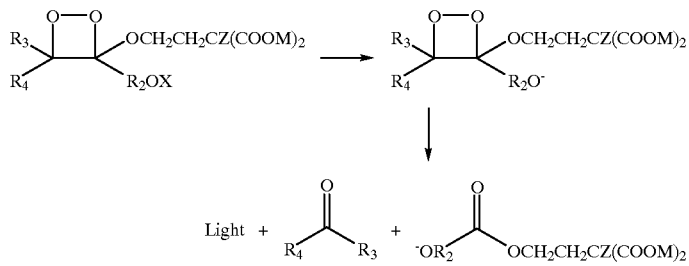

When M is H it is recognized that the respective dioxetane compound will preferably only be used under conditions of pH where the carboxylic acid functions are ionized, i.e. pH≧about 7. Preferably M is an alkali metal ion, most preferably a sodium ion.

The groups $R_3$ and $R_4$ in another embodiment are combined together in a cyclic or polycyclic alkyl group $R_5$ which is spiro-fused to the dioxetane ring, containing 6 to 30 carbon atoms which provides thermal stability and which can include additional non-hydrogen substituents.

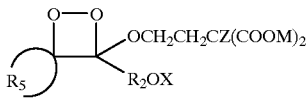

The group $R_5$ is more preferably a polycyclic group, preferably an adamantyl group or a substituted adamantyl group having one or more substituent groups $R_6$ selected from halogens, alkyl, substituted alkyl, alkoxy, substituted alkoxy, carbonyl, carboxyl, phenyl, substituted phenyl, amino and alkylamino groups covalently bonded thereto.

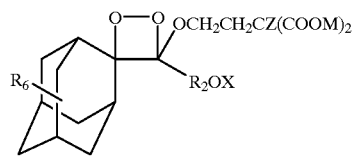

In another preferred embodiment the group $R_2$ is a phenyl or naphthyl group. It is especially preferred that $R_2$ is a phenyl group in which the OX group is oriented meta to the dioxetane ring group as shown below. The phenyl ring may contain additional ring substituents $R_7$ independently selected from halogens, alkyl, substituted alkyl, alkoxy, substituted alkoxy, carbonyl, carboxyl, amino and alkylamino groups. Some exemplary structures include by way of illustration:

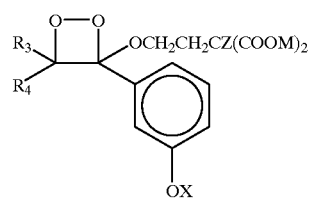

-continued

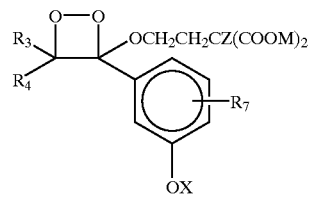

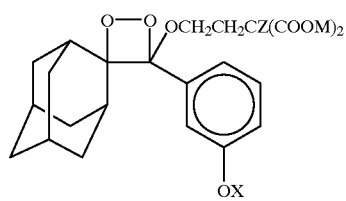

-continued

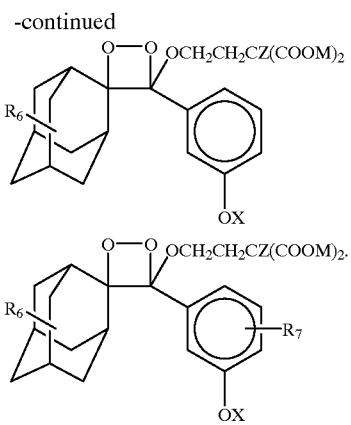

Compounds of the latter two structural formulae in which $R_6$ is H or Cl and $R_7$ is Cl as shown below are recognized as further preferred compounds.

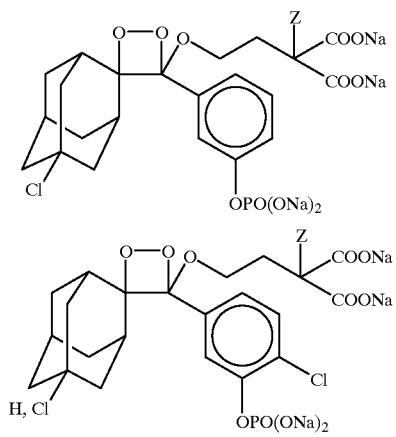

The nature of the OX group is dictated by the triggering agent used in the assay for which it is to be used and may be selected from hydroxyl, $O^-M^+$ wherein M is selected from hydrogen, an alkali metal ion or a quaternary ammonium or phosphonium ion, $OOCR_8$ wherein $R_8$ is selected from the group consisting of alkyl and aryl groups containing 1 to 8 carbon atoms and optionally containing heteroatoms, $OPO_3^{-2}$ salt, $OSO_3^-$ salt, β-D-galactosidoxy and β-D-glucuronidyloxy groups. The OX group is preferably a $OPO_3^{-2}$ salt group.

Dioxetanes of the present invention having the formula:

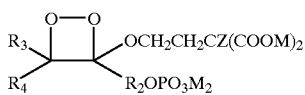

IV wherein $R_2$, $R_3$, $R_4$, M and Z are as described above can be prepared using methods described in Applicants' co-pending application Ser. No. 08/748,107 and other methods known in the art of dioxetane chemistry. For example, a ketone and ester having the formulas below wherein RG is a replaceable atom or group and X' is a replaceable atom or group such as a hydrogen or an alkyl group or a trialkylsilyl group can be coupled by a low-valent titanium reagent to form an intermediate vinyl ether. Removable groups include leaving groups such as halogen atoms selected from Cl, Br and I, sulfates, sulfonates such as tosylate, mesylate and triflate, quaternary ammonium groups, and azide.

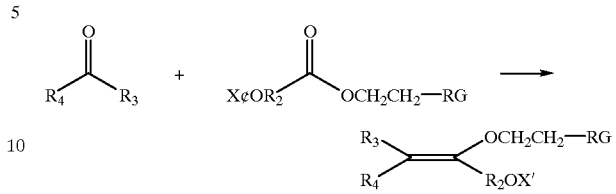

The intermediate vinyl ether is converted in a process of one or more steps to a precursor vinyl ether phosphate salt. It may be desired for synthetic convenience to replace one removable group with another removable group. The group RG is replaced by a $CZ(COOM)_2$ fragment by reaction with a Z-substituted malonate ester and later saponification of the ester groups. The group X' is converted to the group X in the case where X and X' are not identical by removing X' and reacting with a reagent which adds the X group or a protected form of the X group. For example when X' is H and X is $PO_3Na_2$, treatment with base to deprotonate followed by reaction with a phosphorylating agent produces a phosphate triester-protected vinyl ether which is converted to the phosphate salt by hydrolysis of the triester to the disodium salt. In this multi-step process, two or more operations may occur in the same process step, for example hydrolysis of carboxylic esters and phosphate esters can be effected in the same step.

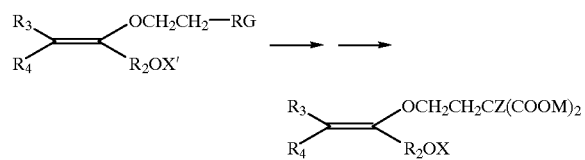

The precursor vinyl ether phosphate salt is directly converted to the dioxetane by known reactions including, for example, addition of singlet oxygen generated by dye sensitization.

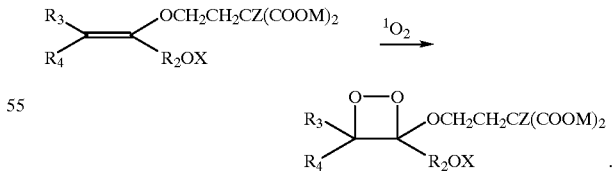

Each of these processes is exemplified by way of illustration in the specific examples below. In particular, Scheme 1 depicts schematically a synthetic pathway used to prepare dioxetanes 3–5 according to the steps described above as disclosed and embodied in the aforementioned 748,107 application.

Scheme 1

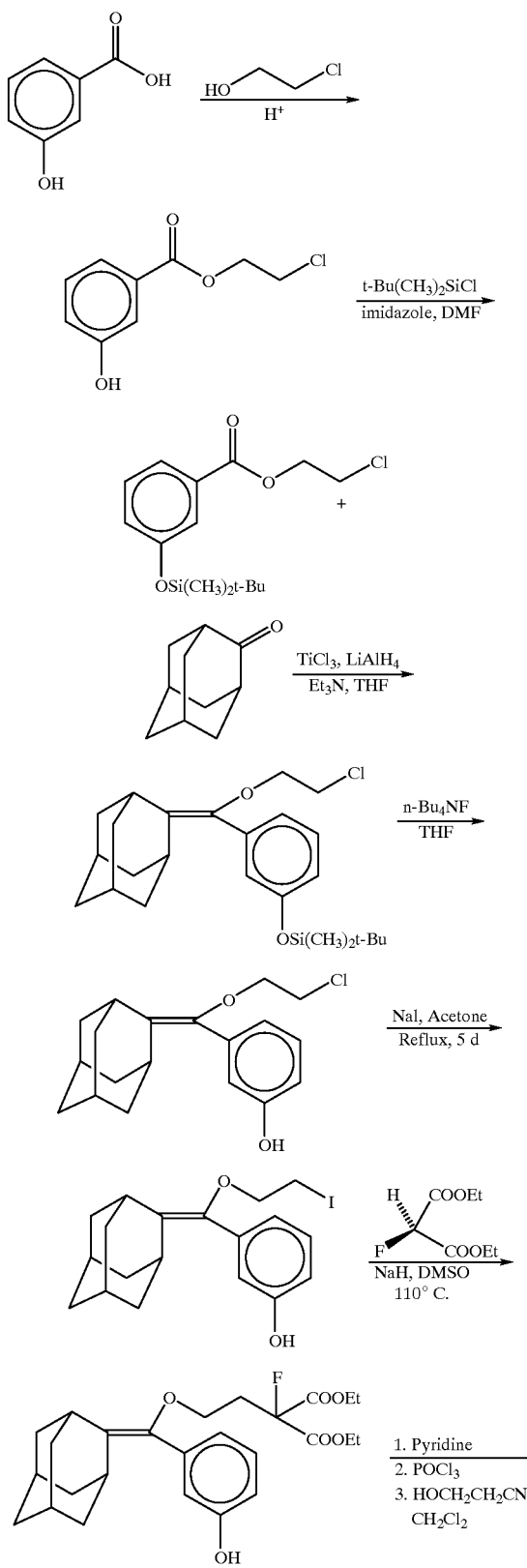

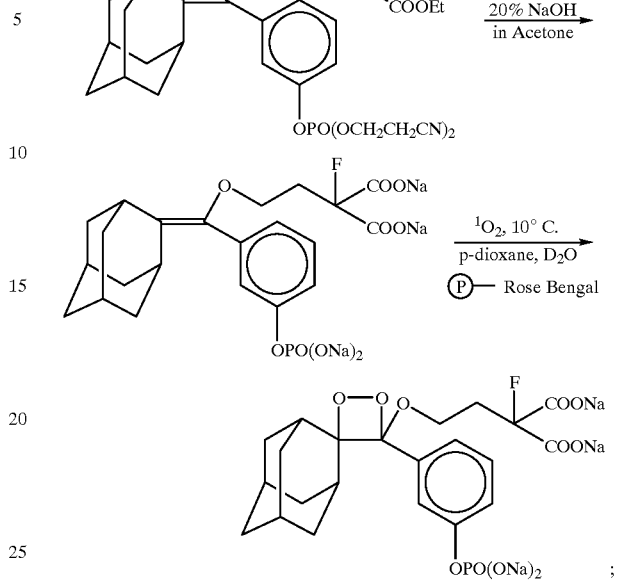

A preferred embodiment of the present invention concerns a process for preparing a dioxetane salt compound of the formula IV:

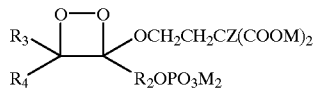

having increased storage stability wherein $R_3$ and $R_4$ are each selected from the group consisting of acyclic, cyclic and polycyclic organic groups which can optionally be substituted with heteroatoms and which can optionally be joined together to form a cyclic or polycyclic ring group spiro-fused to the dioxetane ring, wherein $R_2$ is an aryl ring group selected from the group consisting of phenyl and naphthyl groups which can include additional substituents, wherein Z is selected from the group consisting of halogen atoms and alkyl groups of 1–4 carbons and M is selected from hydrogen, an alkali metal ion or a quaternary ammonium or phosphonium ion comprising the steps of:

a) reacting a first alkene compound having the formula:

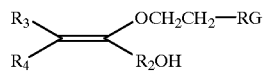

wherein RG is a removable group with a Z-substituted malonate ester and a base to produce a malonate-substituted alkene compound having the formula:

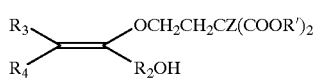

wherein R' is an alkyl group of 1–4 carbons;

b) reacting the malonate-substituted alkene with a phosphorylating reagent having the formula WP(O)Y$_2$ wherein W and Y are each halogen atoms, to form a phosphorylated alkene compound having the formula:

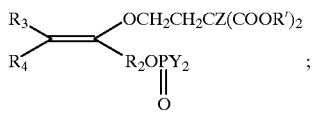
;

c) reacting the phosphorylated alkene compound with a hydroxyl compound of the formula Y'—OH, wherein Y' is selected from substituted or unsubstituted alkyl groups to form a second phosphorylated alkene compound having the formula:

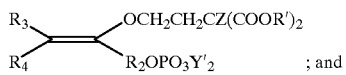
; and d) hydrolyzing the second phosphorylated alkene compound in an aqueous solvent with a base of the formula M—Q wherein Q is a basic anion to form an alkene salt compound having the formula:

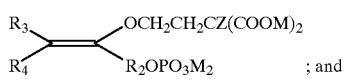
; and e) photooxidizing the alkene salt compound by irradiating a sensitizer in the presence of oxygen and the alkene salt compound in aqueous solution to form the dioxetane salt compound.

It is more preferred that this process is used to prepare a dioxetane in which R$_3$ and R$_4$ are combined together to form a cyclic or polycyclic ring group R$_5$ spiro-fused to the dioxetane ring and the dioxetane salt compound has the formula:

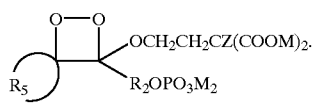

In other preferred processes, the group R$_2$ is a meta-phenyl group, Z is a halogen or an alkyl group having 1–4 carbons atoms, more preferably Z is F or CH$_3$, and M is an alkali metal ion, more preferably M is Na.

It has now been discovered that compounds of formula IV

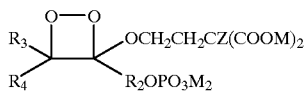

IV having increased storage stability wherein R$_3$ and R$_4$ are each selected from the group consisting of acyclic, cyclic and polycyclic organic groups which can optionally be substituted with heteroatoms and which can optionally be joined together to form a cyclic or polycyclic ring group spiro-fused to the dioxetane ring, wherein R$_2$ is an aryl ring group selected from the group consisting of phenyl and naphthyl groups which can include additional substituents, wherein Z is selected from the group consisting of halogen atoms and alkyl groups of 1–4 carbons, and M is selected from hydrogen, an alkali metal ion or a quaternary ammonium or phosphonium ion can be advantageously prepared by an improved process comprising the steps of:

a) reacting a first alkene compound having the formula:

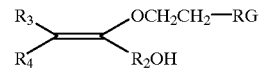

wherein RG is a removable group with a Z-substituted malonate ester and a base to produce a malonate-substituted alkene compound having the formula:

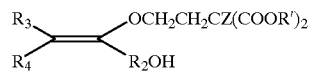

wherein R' is an alkyl group of 1–4 carbons;

b) photooxygenating the malonate-substituted alkene compound by irradiating a sensitizer in the presence of oxygen and the malonate-substituted alkene compound to form a malonate-substituted dioxetane having the formula:

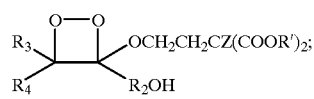

c) reacting the malonate-substituted dioxetane with a phosphorylating reagent having the formula WP(O)Y$_2$ wherein W is selected from halogens and Y is selected from halogen atoms, substituted or unsubstituted alkoxy, aryloxy, aralkyloxy and trialkylsilyloxy groups to form a phosphorylated dioxetane compound having the formula:

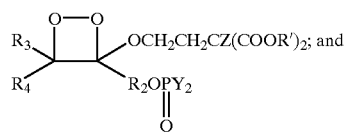

d) hydrolyzing the phosphorylated dioxetane in an aqueous solvent with a base of the formula M—Q wherein Q is a basic anion to form the dioxetane salt compound.

It is more preferred that this process is used to prepare a dioxetane in which R$_3$ and R$_4$ are combined together to form a cyclic or polycyclic ring group R$_5$ spiro-fused to the dioxetane ring and which can contain additional substituents and the dioxetane salt compound has the formula:

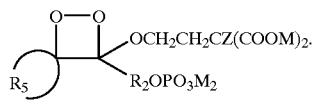

In other preferred embodiments, the process is used to prepare a dioxetane in which the group R$_2$ is a meta-phenyl group which can contain additional substituents, Z is a halogen or an alkyl group having 1–4 carbons atoms, more preferably Z is F or CH$_3$, and M is an alkali metali ion, more preferably M is Na.

The step of reacting the first alkene compound with the Z-substituted malonate ester CHZ(COOR')$_2$ and a base to produce a malonate-substituted alkene compound is generally performed in a polar aprotic solvent such as DMSO, DMF, N,N-dimethylacetamide, N-methylpyrollidone using a poorly nucleophilic base, preferably sodium or potassium hydride. The reaction is preferably performed at an elevated temperature to decrease reaction time, generally between 50 and 150° C., more usually between 80 and 120° C. Removable groups include leaving groups such as halogen atoms selected from Cl, Br and I, sulfates, sulfonates such as tosylate, mesylate and triflate, quaternary ammonium groups, and azide.

In the improved process described herein, the photooxygneation step is performed on the intermediate malonate-substituted alkene instead of photooxygenating a phosphate alkene as the final step of the overall process as described in the 748,107 application. In this step, the malonate-substituted alkene compound bearing a phenol group is dissolved in an organic solvent and irradiated in the presence of a sensitizer and oxygen to form a malonate-substituted dioxetane. Irradiation of a sensitizer and oxygen with light, usually visible light, generates singlet oxygen which reacts with the vinyl ether-type double bond of the malonate-substituted alkene. The sensitizer is can be dissolved in the solvent or, preferably, immobilized on a polymeric particle as is commonly known in the art. Sensitizers useful for generating singlet oxygen include, without limitation, Rose Bengal, methylene blue, eosin, tetraphenylporphyrin (TPP) metal complexes of TPP, especially zinc and manganese and $C_{60}$. Preferred organic solvents include halocarbons such as $CH_2Cl_2$, $CHCl_3$ and $CCl_4$, deuterated halocarbons, low molecular weight ketones and their deuterated analogs, aliphatic and aromatic hydrocarbons and their deuterated analogs. Most preferred is $CH_2Cl_2$. Conducting the photooxygenation in an organic solvent advantageously provides a reaction medium in which the lifetime of singlet oxygen is maximized. This has the effect of significantly decreasing reaction times and permitting the photooxygenation to proceed more readily to completion. Product isolation is facilitated as well, in most cases requiring only a simple filtration of sensitizer and evaporation of solvent.

The step of reacting the malonate-substituted dioxetane with a phosphorylating reagent having the formula $WP(O)Y_2$ wherein W is selected from halogens and Y is selected from halogen atoms, substituted or unsubstituted alkyloxy groups and trialkylsilyloxy groups to form a phosphorylated dioxetane compound is performed in an organic solvent, preferably a halocarbon such as $CH_2Cl_2$ or $CHCl_3$ or an ether such as diethyl ether or tetrahydrofuran (THF) in the presence of an amine base. Useful amine bases include, without limitation, pyridine and triethylamine. When Y is a substituted or unsubstituted alkyloxy group, an aryloxy, aralkyloxy or trialkylsilyloxy group, representative Y groups include, by way of example, alkoxy such as $OCH_3$, $OCH_2CH_3$, and the like, substituted alkoxy such as cyanoethoxy ($OCH_2CH_2CN$) or trimethylsilylethoxy ($OCH_2CH_2Si(CH_3)_3$), phenoxy, substituted phenoxy, benzyloxy, trimethylsilyloxy and others as are generally known to the skilled organic chemist. The two groups Y can also be combined together as a single group such as ethylenedioxy as occurs in the reagent

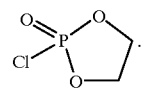

Preferred groups Y are cyanoethoxy groups. In a more preferred embodiment, Y is a halogen, preferably Y and W are both Cl.

The phosphorylation step is performed in solution at a temperature in the range of about −78° C. to about 25° C. A temperature of about 0–5° C. is particularly convenient. The phosphorylating agent $WP(O)Y_2$ is added in a controlled fashion so as not to cause the reaction solution to become hot. The phosphorylating reagent is preferably accompanied by an amine base during the addition, preferably pyridine.

The hydrolysis or deprotection step is accomplished by hydrolyzing the phosphorylated dioxetane in an aqueous solvent with a base of the formula M—Q wherein Q is a basic anion in a quantity sufficient to cause removal of the protecting groups Y and R' to form the dioxetane salt compound. The solvent can comprise water, an aqueous buffer or a mixture of water and one or more organic solvents. Preferred orgnaic solvents are water-miscible solvents such as methanol, ethanol, acetone and THF. Four equivalents of the base are typically required, however for convenience, an excess can be employed. Removal of the protecting groups can be performed sequentially or simultaneously. Depending on the particular groups Y and R' and the base it may or may not be possible to isolate partially hydrolyzed intermediates.

The choice of the basic deprotecting agent will be determined, in part, by the nature of the groups Y and R' to be removed. The deprotecting agent must also not cause undesired side reactions such as hydrolysis of the vinyl ether group in the process where the vinyl ether phosphate salt is first prepared or decomposition of the dioxetane ring group in the process where the protected dioxetane is prepared. Preferred deprotecting agents include organic and inorganic bases such as sodium hydroxide, potassium hydroxide, potassium carbonate, sodium methoxide, sodium ethoxide, potassium t-butoxide, ammonia, ammonium hydroxide and the like. Other preferred deprotecting agents include nucleophilic agents such as cyanide ion, fluoride ion.

In another embodiment, the step of reacting the malonate-substituted dioxetane compound with the phosphorylating reagent comprises the steps of:

a) reacting the malonate-substituted dioxetane compound with a phosphorylating reagent having the formula $WP(O)Y'_2$ herein W and Y' are each halogen atoms to form a dioxetane phosphoryl halide compound having the formula;

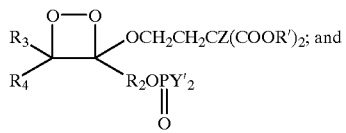

b) reacting the dioxetane phosphoryl halide compound with a hydroxyl compound of the formula Y—OH, wherein Y is selected from substituted or unsubstituted alkyl groups to form the phosphorylated dioxetane compound.

The dioxetane phosphoryl halide compound is converted to the phosphorylated dioxetane compound by reaction with at least two equivalents of a hydroxyl compound Y—OH and preferably with an excess. Exemplary compounds which can serve as the hydroxyl compound Y—OH include, without limitation, lower alcohols such as methanol and ethanol, substituted lower alcohols such as 3-hydroxypropionitrile ($HOCH_2CH_2CN$) and 2-trimethylsilylethanol, phenol, substituted phenols, benzyl alcohol and others as are generally known.

In another aspect, the present invention relates to synthetic intermediates used in the processs for preparing the present dioxetanes. In particular the following novel alkene intermediate compounds are useful.

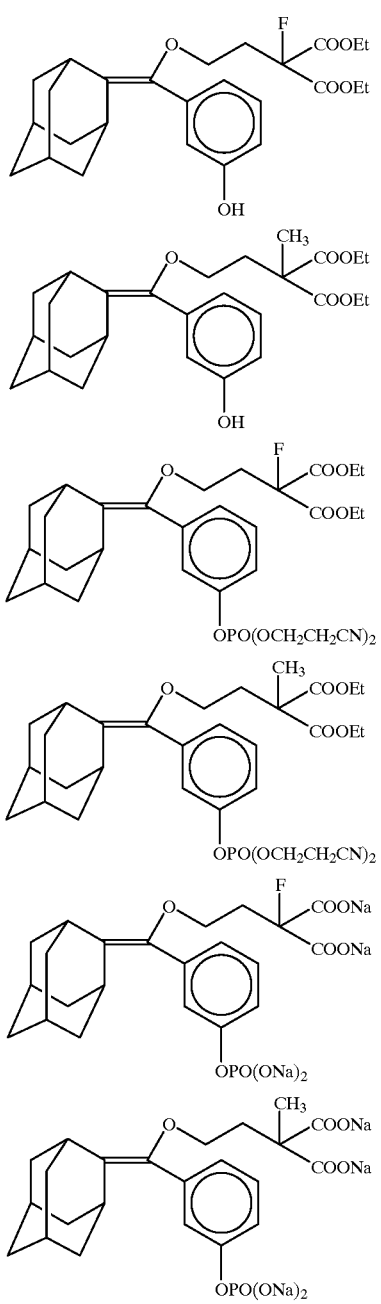
Additionally the following novel dioxetane compounds are useful as synthetic intermediates in the preparation of the present dioxetane compounds.
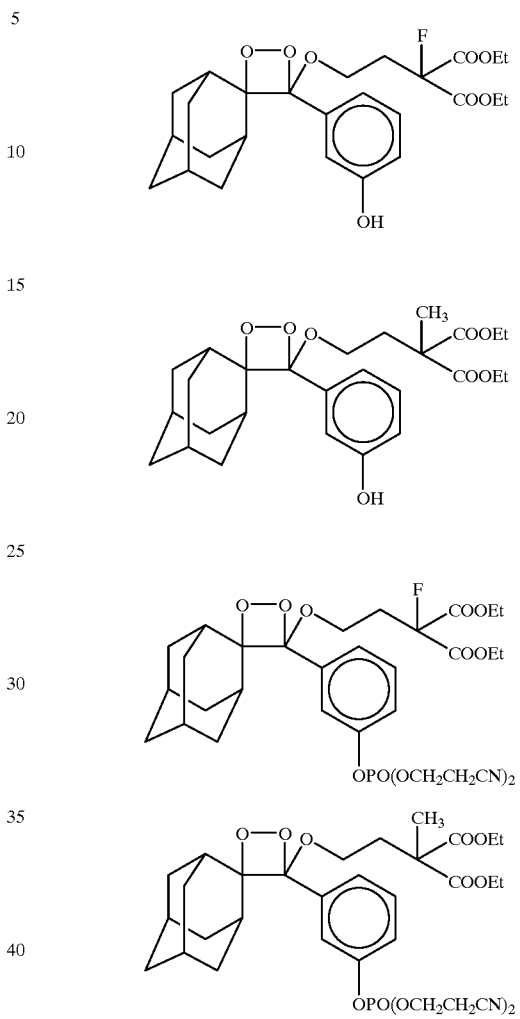
An exemplary synthesis of a dioxetane of the present invention by this improved process is shown in Scheme 2.
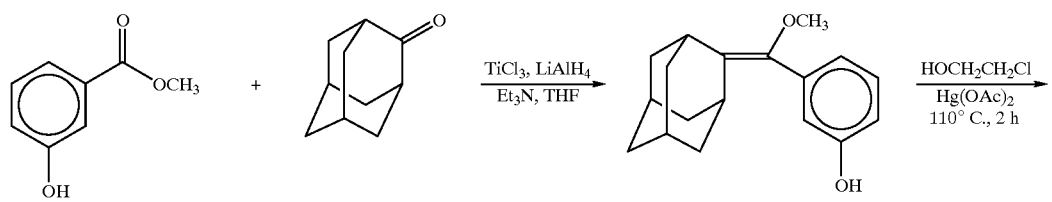

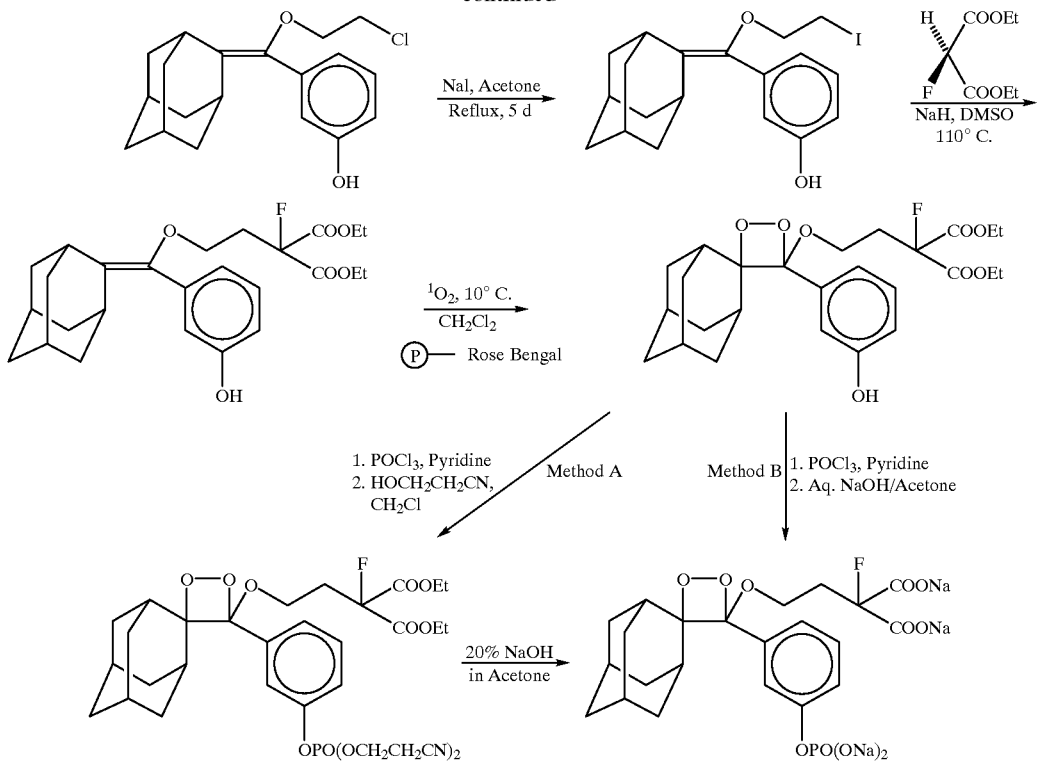

The starting material (precursor alkene) in the above described synthetic processes having the formula:

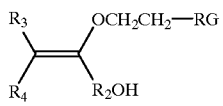

wherein RG is a removable group can be prepared by methods known in the art. In one method, the vinyl ether function is prepared by Ti-mediated coupling of a ketone $R_3R_4C=O$ and an ester $HOR_2COOCH_2CH_2-G$ as described in U.S. Pat. Nos. 4,983,779 and 4,982,192 wherein G is a group which may be identical with RG or may be a group which can be replaced by RG or converted into RG. An exemplary synthetic process in which RG is an iodine atom and G is a chlorine atom is presented hereinbelow. It is further recognized that, for convenience, the ester component of the coupling reaction may be used in protected form in which the hydroxyl group is present in a masked form such as a silyl ether or an alkyl ether. After the coupling reaction, the free hydroxyl group is then liberated using standard synthetic means.

It has further been discovered by Applicants that these precuror alkenes can also be prepared by a new process not previously reported for the preparation of this type of vinyl ether. While the foregoing Ti-mediated process requires the preparation of individual ester compounds bearing the G or RG group, adding additional complexity and cost, the new process utilizes a common vinyl ether intermediate which can be prepared from commercially available starting materials.

An example of a reaction for preparing the precursor alkene by the new process is depicted below. A lower alkyl vinyl ether compound, wherein lower alkyl, $R_9$, here indicates a $C_1$-$C_4$ straight or branched alkyl group, is reacted with a catalytic amount of a mercury salt in the presence of at least one mole equivalent of another alcohol $R_{10}$—OH, e.g. one having the formula $HOCH_2CH_2G$, to produce the desired precursor alkene.

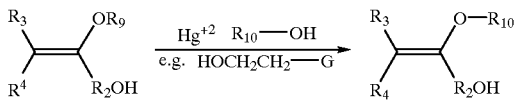

The conversion of unsubstituted vinyl ethers having the formula $CH_2=CHOR_a$ to other unsubstituted vinyl ethers having the formula $CH_2=CHOR_b$ is known and described, e.g. in W. H. Watanabe and L. E. Conlon, J. Am. Chem.Soc. 79, 2828 (1957), the preparation by a mercury salt-catalyzed reaction of trisubstituted alkenes used in the present processes has not been reported to the best of Applicants' knowledge.

In this reaction process, $R_3$ and $R_4$ are each selected from acyclic, cyclic and polycyclic organic groups which can optionally be substituted with heteroatoms and which can optionally be joined together to form a cyclic or polycyclic ring group $R_5$ spiro-fused to the dioxetane ring, $R_2$ is an aryl ring group selected from phenyl and naphthyl groups which can include additional substituents. An example of the use of this mercury-catalyzed reaction for the preparation of an alkene precursor to a dioxetane of the invention is

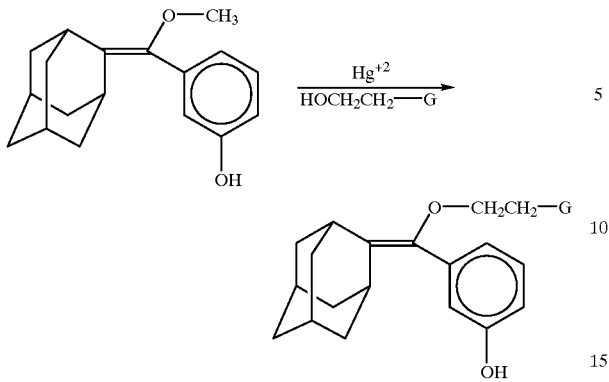

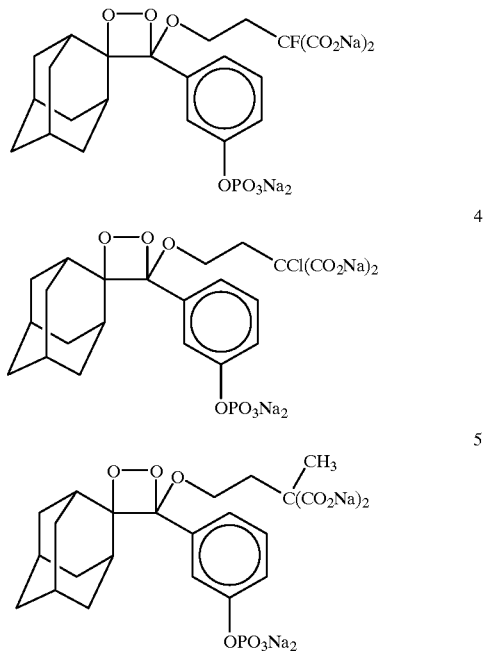

wherein G is a chlorine atom. The mercury salt is any Hg(II) salt which functions to catalyze the vinyl ether groups and is preferably a salt of a weak acid such as acetate or trifluoroacetate. The mercury salt is used in catalytic quantitity, typically from 0.01 to 0.5 moles per mole of alkene, more typically from 0.05 to 0.25. The alcohol component $R_{10}$—OH can be any alkanol, substituted alkanol, benzyl alcohol, unsaturated alcohol, such as allyl alcohol. The alcohol is used in excess, at least two moles per mole of alkene and preferably at least 5 moles per mole of alkene. In a preferred process, the alcohol is used as the reaction solvent. The reaction is typically but not necessarily conducted above ambient temperature up to the boiling point of the solvent. Preferable reaction temperatures are in the range of about 70–120° C.

Additional solvents for purposes of improving the solubility of reactants or altering polarity or boiling point can be used.

It is recognized that while the mercury-catalyzed vinyl ether exchange reaction described above will find particular use in the preparation of intermediates used for the further elaboration to water soluble tri-substituted dioxetane of the present invention, it is more generally applicable to the preparation of a wide variety of alkene or vinyl ether compounds.

Specific Embodiments

A fluoro-substituted analog of dioxetane 1, identified as 3, a chloro-substituted analog 4 and a methyl-substituted analog 5 have been prepared and their storage stability evaluated over several weeks. Storage stability of a solution of 1 was measured for comparison. All solutions were prepared with the same composition, differing only in the identity of the dioxetane. Stability was evaluated by chemiluminescent enzyme assay with a fixed volume of test solution and fixed limiting amount of alkaline phosphatase and measuring the plateau light intensity at 25° C. Unexpectedly, aqueous solutions containing dioxetanes 3 and 5 were substantially more stable than 1, while dioxetane 4 was not. Solutions of dioxetanes 3 or 5 underwent essentially no decomposition after four weeks at 25° C. Surprisingly, the storage stability of dioxetane 4 was actually worse than that of 1.

The reasons for this difference in the properties of these four dioxetanes are not presently understood. It is particularly significant that dioxetanes 3 and 4 should show such marked difference in storage stability when they differ structurally only by having different halogen substituents. Applicants are aware of no teachings in the art of dioxetane chemistry to explain or predict these results.

Furthermore, tests on dioxetane 3, showed that, like dioxetane 1, it caused no carryover in the capsule chemistry assay system. Dioxetanes such as 3 and 5 bearing a substituent containing two carboxylate groups and either a fluorine atom or a lower alkyl group and compositions containing such dioxetanes are therefore superior to other known dioxetanes and compositions for use in capsule chemistry analysis systems.

In another aspect of the invention, compositions providing enhanced chemiluminescence are provided. Enhanced compositions are advantageous in assays requiring the highest analytical sensitivity. Increasing the chemiluminescence efficiency of the dioxetane decomposition reaction while maintaining or reducing extraneous light emission from spontaneous dioxetane decomposition is one manner in which sensitivity can be enhanced or improved.

The present invention, therefore, also relates to compositions comprising a cationic enhancer and a stable 1,2-dioxetane as described above having increased storage stability which can be triggered to generate chemiluminescence. Such compositions for providing enhanced chemiluminescence comprise a dioxetane as described above in an aqueous solution, and a non-polymeric cationic enhancer substance which increases the quantity of light produced by reacting the dioxetane with the activating agent compared to the amount which is produced in the absence of the enhancer. It is preferred that the enhancer substance is a dicationic surfactant of the formula:

wherein each of A is independently selected from P and N atoms and wherein Link is an organic linking group containing at least two carbon atoms selected from the group consisting of substituted and unsubstituted aryl, alkyl, alkenyl and alkynyl groups and wherein Link may contain heteroatoms and wherein R is selected from lower alkyl or aralkyl containing 1 to 20 carbon atoms and wherein Y is an anion. It is especially preferred that the enhancer substance is a dicationic surfactant having the formula:

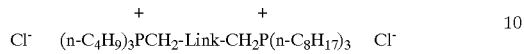

and wherein link is phenylene.

Compositions of the present invention for providing enhanced chemiluminescence may optionally contain at least one fluorescer as a supplementary enhancer. Fluorescers useful are those compounds which are capable of increasing the quantity of light produced through energy transfer. Anionic fluorescers are particularly effective it is believed due to favorable electrostatic interactions with the cationic enhancer. Particularly preferred fluorescers are anionic compounds and include, without limitation, pyranine and fluorescein.

In order to more fully describe the various aspects of the present invention, the following non-limiting examples describing particular embodiments are presented for purposes of illustration of the invention.

EXAMPLES

Example 1

Preparation of Dioxetane 1

The dioxetane [4-(3,3-biscarboxy)propoxy)-4-(3-phosphoryloxyphenyl)]spiro[1,2-dioxetane-3,2'-tricyclo [3.3.1.1$^{3,7}$]decane], tetrasodium salt was prepared by the sequence of reactions described in Applicants' U.S. Pat. No. 5,631,167. The synthesis up to the intermediate alkene [(3-hydroxyphenyl)-(2-iodoethoxy)-methylene]tricyclo [3.3.1.1$^{3,7}$]decane was conducted essentially as described in U.S. Pat. Nos. 5,013,827 and 5,068,339.

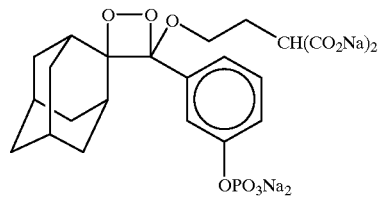

1

Example 2

Preparation of Dioxetane 2

The dioxetane [4-(3-carboxypropoxy)-4-(3-phosphoryloxyphenyl)]spiro[1,2-dioxetane-3,2'-tricyclo [3.3.1.1$^{3,7}$]-decane] (2) was prepared by the sequence of reactions described in Applicants' U.S. Pat. No. 5,631,167. The synthesis up to the intermediate alkene [(3-carboxypropoxy)-(3-hydroxyphenyl)methylene]-tricyclo [3.3.1.1$^{3,7}$]decane was conducted essentially as described. in U.S. Pat. Nos. 5,013,827 and 5,068,339.

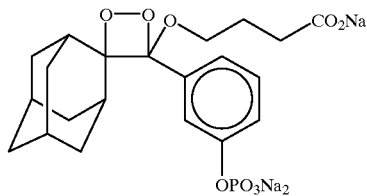

2

Example 3

Preparation of Dioxetane 3

This dioxetane was prepared by the sequence of reactions described below. The synthesis up to the intermediate alkene [(3-hydroxyphenyl)-(2-iodoethoxy)methylene]tricyclo [3.3.1.1$^{3,7}$]decane was conducted as described in Example 1.

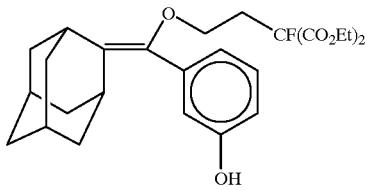

(a) Synthesis of [((3,3-biscarboethoxy)-3-fluoropropoxy)-(3-hydroxyphenyl)methylenetricyclo [3.3.1.1$^{3,7}$]decane. Sodium hydride (75 mg of a 60% dispersion in oil) was washed free of oil with hexane, dried under vacuum and added to 4 mL of anhydrous DMSO. Diethyl fluoromalonate (0.3 g) was added and the suspension stirred under Ar for 15 min. A solution of the iodoethoxy alkene (0.5 g) in 5 mL of anhydrous DMSO was added to the reaction mixture. The reaction was heated to 100° C. and stirred for 2 h. After cooling, the mixture was diluted with 30 mL of ethyl acetate. The ethyl acetate solution was extracted 3–4 times with water, dried and evaporated. The crude material was chromatographed using 5–20% ethyl acetate in hexane. The desired compound (0.25 g) was obtained in 45% yield: $^1$H NMR (CDCl$_3$) δ1.28 (t,6H), 1.66–1.95 (m,12H), 2.45 (t,1H), 2.52 (t,1H), 2.67(br s,1H), 3.20 (br s,1H), 3.52(t, 2H), 4.23–4.30 (q,4H), 6.74–7.22 (m,4H).

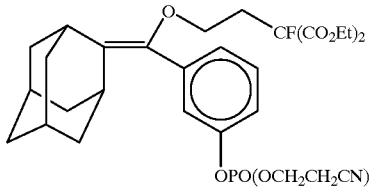

(b) Synthesis of [((3,3-biscarboethoxy)-3-fluoropropoxy-(3-( bis-(2-cyanoethyl)phosphoryloxy)phenyl)methylene] tricyclo[3.3.1.1$_{3,7}$]decane. A flask containing 10 mL of CH$_2$Cl$_2$ under a layer of argon was cooled in an ice bath. Pyridine (1.71 mL) was added followed by slow addition of POCl$_3$ (0.61 mL) and stirring continued for 15 min. A solution of the alkene (0.972 g) from step (a) in 10 mL of CH$_2$Cl$_2$ was added dropwise. The ice bath was removed and the solution stirred for 2.5 h. To this solution was added 1.71 mL of pyridine and 1.44 mL of 2-cyanoethanol. The reaction mixture was stirred for 12–15 h resulting in formation of a white precipitate. The mixture was diluted with CH$_2$Cl$_2$ and washed with 4×50 mL of water. The CH$_2$Cl$_2$ extract was dried and evaporated. The crude product was purified by chromatography using 75% ethyl acetate in hexane. A total of 1.2 g of an oil (88%) was obtained: $^1$H NMR (CDC$_1$) δ1.29 (s,6H), 1.79–1.97 (m,12H), 2.46–2.53 (2t,2H), 2.63 (br s,1H), 2.83 (t,4H), 3.20 (br s,1H), 3.50 (t,2H), 4.24–4.31 (q,4H), 4.35–4.51 (m,4H), 7.13–7.36 (m,4H); $^{31}$P NMR (CDCl$_3$) δ–9.49 (p).

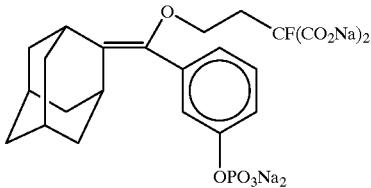

c) Synthesis of [(3,3-biscarboxy-3-fluoropropoxy)-(3-phosphoryloxyphenyl)methylene]tricyclo[3.3.1.1$^{3,7}$]-decane, tetrasodium salt. The alkene (1.2 g) from step (b) was dissolved in 20 mL of acetone. A solution of 297 mg of sodium hydroxide in 4 mL of water was added. The solution was stirred over night during which time a precipitate formed. The liquid was decanted and the solid washed with 10×5 mL of acetone. After drying under vacuum, a white solid (1.0 g) was obtained: $^1$H NMR (D$_2$O) δ1.75–1.89 (m,12H), 2.29 (t,2H), 2.37 (t,2H), 2.57 (br s,1H), 3.12 (br s,1H), 3.56 (t,2H), 6.99–7.30 (m,4H); $^{31}$P NMR (D$_2$O) δ0.69 (s).

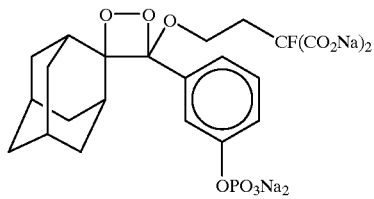

(3)

(d) Synthesis of [4-(3,3-biscarboxy-3-fluoropropoxy)-4-(3-phosphoryloxyphenyl)]spiro[1,2-dioxetane-3,2'-tricyclo[3.3.1.1$^{3,7}$]decane], tetrasodium salt (3). The alkene (348.6 mg) from step (c) was dissolved in 10 mL of D$_2$O. Polymer-bound Rose Bengal (500 mg) was suspended in 10 mL of p-dioxane and added to the water solution. The reaction mixture was cooled to 5–8° C., oxygen bubbling was started and the mixture irradiated with a sodium lamp through a 5 mil KAPTON filter. After a total of 2.5 h, the polymer beads were filtered off and the solution was evaporated to dryness producing a white solid (3). $^1$H NMR (D$_2$O) δ0.93–1.79 (m, 12H), 2.19 (br s,1H), 2.41–2.49 (m,2H), 2.97 (br s,1H), 3.40–3.49 (m,2H), 7.19–7.42 (m,4H); $^{31}$P NMR (D$_2$O) δ0.575 (s).

Example 4

Preparation of Dioxetane 4

This dioxetane was prepared by the sequence of reactions described below. The synthesis up to the intermediate alkene [(3-hydroxyphenyl)-(3,3-biscarboethoxy) propoxymethylene]tricyclo[3.3.1.1$^{3,7}$]decane was conducted as described in Example 1.

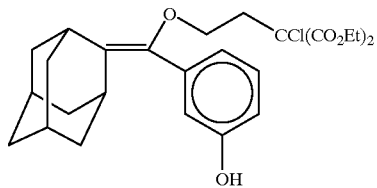

(a) Synthesis of [((3,3-biscarboethoxy)-3-chloropropoxy)-(3-hydroxyphenyl)methylenetricyclo[3.3.1.1$^{3,7}$]decane. A solution of (3,3-biscarboethoxypropoxy)-(3-hydroxyphenyl)methylenetricyclo[3.3.1.1$^{3,7}$]decane (1.2 g) in 10 mL of dry THF was added to a 2.4 eq. of LDA in 25–30 mL of dry THF at –78° C. under argon. The reaction was stirred for 30 min at –78° C. and treated with a solution of N-chlorosuccinimide (0.58 g) in 15 mL of dry THF. The reaction was allowed to warm to room temperature over an hour and stirred for an additional hour. The THF was removed in vacuo and the residue dissolved in 100 mL of ethyl acetate. The organic solution was washed with water, dried and evaporated. The crude material was separated by column chromatography. $^1$H NMR (CDCl$_3$) δ1.23 (t,6H), 1.7–2.00 (m,12H), 2.57 (t,2H), 2.65 (br s,1H), 3.2 (br s,1H), 3.56 (t,2H), 4.22 (q,4H), 6.65–7.25 (m,4H).

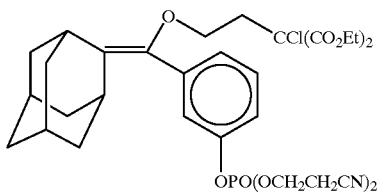

(b) Synthesis of [((3,3-biscarboethoxy)-3-chloropropoxy-(3-(bis-(2-cyanoethyl)phosphoryloxy)phenyl)methylene]tricyclo[3.3.1.1$^{3,7}$]decane. A flask containing 25 mL of CH$_2$Cl$_2$ under a layer of argon was cooled in an ice bath. Pyridine (1.5 g) was added followed by slow addition of POCl$_3$ (1.82 g) and stirring continued for 15 min. A solution of the alkene (1.5 g) from step (a) and 1.5 g of pyridine in 25 mL of CH$_2$Cl$_2$ was added dropwise. The ice bath was then removed and the solution stirred for 1 h. The solution was again cooled with an ice bath and treated sequentially with 3.0 g of pyridine and 2.8 g of 2-cyanoethanol. The reaction mixture was stirred for 12–15 h resulting in formation of a white precipitate. The mixture was diluted with CH$_2$Cl$_2$ and washed with water. The CH$_2$Cl$_2$ extract was dried and evaporated. The crude product was purified by chromatography using 50% ethyl acetate in hexane. A total of 1.4 g of product was obtained an oil: $^1$H NMR (CDCl$_3$) δ1.278 (t,6H), 1.80–1.97 (m,12H), 2.565 (t,2H), 2.63 (br s,1H), 2.826 (t,4H), 3.20 (br s,1H), 3.556 (t,2H), 4.271 (q,4H), 4.40–4.47 (m,4H), 7.15–7.36 (m,4H).

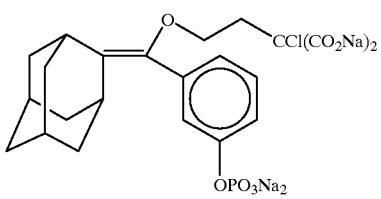

(c) Synthesis of [(3,3-biscarboxy-3-chloropropoxy)-(3-phosphoryloxyphenyl)methylene]tricyclo[3.3.1.1$^{3,7}$]-decane, tetrasodium salt. The alkene (0.9 g) from step (b)

was dissolved in 25 mL of acetone. A solution of 0.22 g of sodium hydroxide in 3 mL of water was added. The solution was stirred over night during which time a precipitate formed. The liquid was decanted and the solid triturated with acetone. The white solid was filtered, washed further with acetone and dried under vacuum: $^1$H NMR (D$_2$O) δ1.77–1.92 (m,12H), 2.422 (t,2H), 2.59 (br s,1H), 3.15 (br s,1H), 3.635 (t,2H), 7.02–7.33 (m,4H).

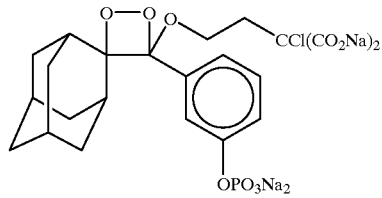

4

(d) Synthesis of [4-(3,3-biscarboxy)-3-chloropropoxy)-4-(3-phosphoryloxyphenyl)]spiro[1,2-dioxetane-3,2'-tricyclo[3.3.1.1$^{3,7}$]decane], tetrasodium salt (4). The alkene (35 mg) from step (c) was dissolved in 1.0 mL of D$_2$O. Polymer-bound Rose Bengal (500 mg) was soaked in 1.0 mL of p-dioxane-d$_8$ for 5 min and then added to the water solution. The reaction mixture was cooled to 0° C., oxygen bubbling was started and the mixture irradiated with a sodium lamp through a 5 mil KAPTON filter for 45 min to produce 4 as determined by NMR. The mixture was filtered and the solution diluted in buffer for enzyme assay: $^1$H NMR (D$_2$O) δ1.05–1.96 (m, 12H), 2.19 (br s,1H), 2.60–2.62 (m,2H), 3.07 (br s,1H), 3.56–3.58 (m,2H), 7.25–7.44 (m,4H).

Example 5

Preparation of Dioxetane 5

This dioxetane was prepared by the sequence of reactions described below. The synthesis up to the intermediate alkene [(3-hydroxyphenyl)-(2-iodoethoxy)methylene]tricyclo[3.3.1.1$^{3,7}$]decane was conducted as described in Example 1.

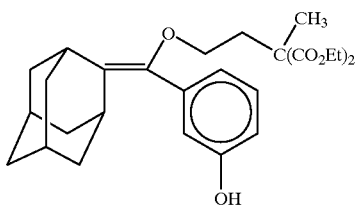

(a) Synthesis of [((3,3-biscarboethoxybutoxy)-(3-hydroxy-phenyl)methylenetricyclo[3.3.1.1$^{3,7}$]decane. Sodium hydride (0.866 g of a 60% dispersion in oil) was washed free of oil with hexane, dried under vacuum and added to 15 mL of anhydrous DMSO. Diethyl methylmalonate (2.4 g) was added and the suspension stirred under Ar for 15 min. A solution of the iodoethoxy alkene (2.8 g) in 15 mL of anhydrous DMSO was added to the reaction mixture. The reaction was heated to 100° C. and stirred for 2 h. After cooling, the mixture was diluted with 30 mL of ethyl acetate. The ethyl acetate solution was extracted 3–4 times with water, dried and evaporated. The crude material was chromatographed using 5–20% ethyl acetate in hexane. The desired compound (0.80 g) was obtained in 25% yield: $^1$H NMR (CDCl$_3$) δ1.208 (t,6H), 1.347 (s,3H), 1.76–1.96 (m,12H), 2.20 (t,2H), 2.66 (br s,1H), 3.20 (br s,1H), 3.41 (t, 2H), 4.09–4.17 (q,4H), 6.78–7.26 (m,4H).

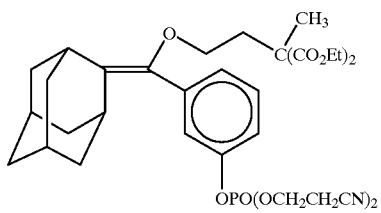

(b) Synthesis of [((3,3-biscarboethoxybutoxy-3-(bis-(2-cyanoethyl)phosphoryloxy)phenyl)methylene]tricyclo[3.3.1.1$^{3,7}$]decane. A flask containing 15 mL of CH$_2$Cl$_2$ under a layer of argon was cooled in an ice bath. Pyridine (1.38 g) was added followed by slow addition of POCl$_3$ (0.8 g) and stirring continued for 15 min. A solution of the alkene (0.8 g) from step (a) in 15 mL of CH$_2$Cl$_2$ was added dropwise. The ice bath was removed and the solution stirred for 1 h. To this solution was added 1.38 g of pyridine and 1.24 g of 2-cyanoethanol. The reaction mixture was stirred for 12–15 h resulting in formation of a white precipitate. The mixture was diluted with CH$_2$Cl$_2$ and washed with 4×50 mL of water. The CH$_2$Cl$_2$ extract was dried and evaporated. The crude product was purified by chromatography using 75% ethyl acetate in hexane. A total of 0.55 g of an oil (50%) was obtained: $^1$H NMR (CDCl$_3$) δ1.208 (t,6H), 1.34 (s,3H), 1.78–1.97 (m,12H), 2.18 (t,2H), 2.61 (br s,1H), 2.81 (t,4H), 3.21 (br s,1H), 3.41 (t,2H), 4.09–4.16 (q,4H), 4.37–4.46 (m,4H), 7.14–7.34 (m,4H).

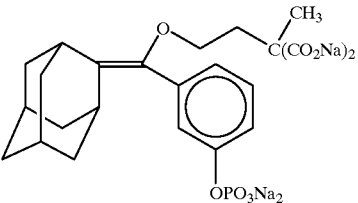

(c) Synthesis of [(3,3-biscarboxybutoxy)-(3-phosphoryloxyphenyl)methylene]tricyclo[3.3.1.1$^{3,7}$] decane, tetrasodium salt. The alkene (0.47 g) from step (b) was dissolved in 14 mL of acetone. A solution of 0.117 g of NaOH in 1.5 mL of water was added. The solution was stirred over night during which time a precipitate formed. The liquid was decanted and the solid washed with 10×5 mL of acetone. After drying under vacuum, a white solid (0.383 g, 92%) was obtained: $^1$H NMR (D$_2$O) δ1.09 (s,3H), 1.75–1.90 (m,12H), 2.00 (t,2H), 2.57 (br s,1H), 3.13 (br s,1H), 3.47 (t,2H), 7.01–7.29 (m,4H).

(5)

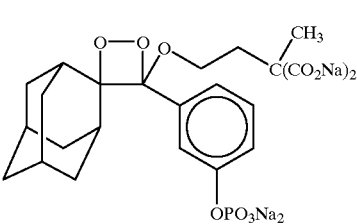

(d) Synthesis of [4-(3,3-biscarboxybutoxy)-4-(3-phosphoryloxyphenyl)]spiro[1,2-dioxetane-3,2'-tricyclo[3.3.1.1$^{3,7}$]-decane], tetrasodium salt (5). The alkene (65 mg) from step (c) was dissolved in 3 mL of D$_2$O. Polymer-bound Rose Bengal (35 mg) was suspended in 3 mL of p-dioxane and added to the water solution. The reaction mixture was cooled to 5–8 ° C., oxygen bubbling was started and the mixture irradiated with a sodium lamp through a 5 mil KAPTON filter for 1 h to produce (5). The polymer beads were filtered off and the solution used for preparing stock solutions for testing. $^1$H NMR (D$_2$O) δ0.92–1.33 (m, 5H), 1.38–2.21 (m, 13H), 2.92 (br s,1H), 3.19–3.32 (m,2H), 7.14–7.73 (m,4H).

Example 6
Alternative Preparation of Dioxetane 3

The dioxetane was prepared by the sequence of reactions described below using [(3-hydroxyphenyl) methoxymethylenetricyclo[3.3.1.1$^{3,7}$]decane as starting material. This compound can be prepared as described in U.S. Pat. No. 4,983,779.

(a) The alkene [(3-hydroxyphenyl) methoxymethylenetricyclo[3.3.1.1$^{3,7}$]decane (12 g) was added to 100 mL of 2-chloroethanol and stirred. A catalytic amount of Hg(OAc)$_2$ (2.8 g) was then added to the mixture under an argon atmosphere. The reaction was stirred for 5 h at 110° C. After cooling to room temperature, the chloroethanol was remove under vacuum. The solid was dissolved in EtOAc and washed with water. The EtOAc layer was dried over Na$_2$SO$_4$ and evaporated to produce [(3-hydroxyphenyl)-(2-chloroethoxy)methylene]tricyclo[3.3.1.1$^{3,7}$]decane.

(b) Replacement of the chlorine atom in the above compound with an iodine atom was conducted essentially as described in U.S. Pat. Nos. 5,013,827 and 5,068,339.

(c) Synthesis of [(3-hydroxyphenyl)-(3,3-biscarboethoxy)-3-fluoropropoxymethylene]tricyclo[3.3.1.1$^{3,7}$]decane from [(3-hydroxyphenyl)-(2-iodoethoxy) methylene]tricyclo[3.3.1.1$^{3,7}$]decane is described in Example 3 above.

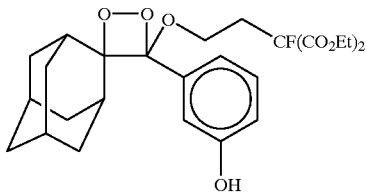

(d) The fluoromalonate alkene from step (c) (0.375 g) was photooxygenated with ca. 1 mg of methylene blue in 15 mL of CH$_2$Cl$_2$. After cooling the solution to –78° C. with O$_2$ bubbling, the solution was irradiated with a sodium lamp through a 5 mil KAPTON filter for 45 min and then allowed to warm to room temperature. The CH$_2$Cl$_2$ was evaporated and the residue chromatographed using from 0–5% EtAc in CH$_2$Cl$_2$ as eluent to produce [4-(3,3-biscarboethoxy-3-fluoropropoxy)-4-(3-hydroxyphenyl)]spiro[1,2-dioxetane-3,2'-tricyclo[3.3.1.1$^{3,7}$]-decane]: $^1$H NMR (CDCl$_3$) δ0.97–1.02 (m,1H), 1.21–1.33 (m,7H), 1.45–1.91 (m,10H), 2.23 (br s,1H), 2.48–2.80 (m,2H), 2.96 (br s,1H), 3.35–3.44 (m,1H), 3.65–3.75 (m,1H), 4.21–4.40 (m,4H), 6.85–7.40 (m,4H).

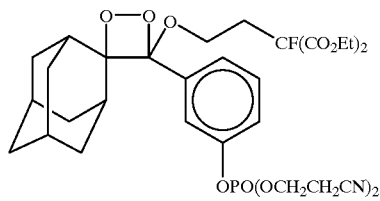

(e) The dioxetane from the previous step was phosphorylated by the following process. A solution of 2 mL of anhydrous pyridine and 10 mL of CH$_2$Cl$_2$ under argon was cooled to 0° C. and a solution of 0.424 g of POCl$_3$ in 10 mL of CH$_2$Cl$_2$ was added dropwise. After 15 min, a solution of 0.424 g of the dioxetane in 10 mL of CH$_2$Cl$_2$ was added dropwise. The solution was allowed to warm to room temperature and stirred for 4 h. The solution was again cooled to 0° C. and a solution of 0.75 g of cyanoethanol in 10 mL of CH$_2$Cl$_2$ was added dropwise. This solution was allowed to warm to room temperature as it was stirred for 2.5 h. After evaporating to dryness, the residue was chromatographed using from 50–100% ethyl acetate in hexanes as eluent. The solvents were then removed in vacuo yielding a colorless oil. The dioxetane was then dissolved in 100 mL of CH$_2$Cl$_2$ and washed three times with type I water. The organic layer was then dried over Na$_2$SO$_4$, filtered, and evaporated to produce the phosphorylated dioxetane: $^1$H NMR (CDCl$_3$) δ0.90–0.95 (m,1H), 1.24–1.33 (m,7H), 1.46–2.20 (m,11H), 2.50–2.86 (m,6H), 2.96 (br s,1H), 3.32–3.41 (m,1H), 3.62–3.73 (m,1H), 4.20–4.48 (m,8H), 7.30–7.70 (m,4H); $^{31}$P (CDCl$_3$) –9.53 (p).

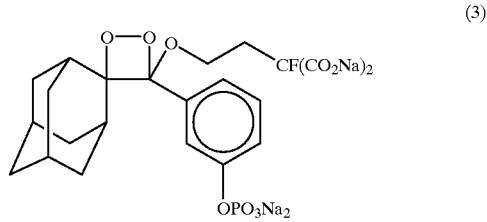

(3)

(f) the alkyl groups were removed by reacting the dioxetane from the previous step with 47.2 mg of NaOH in 1 mL of type I water and 10 mL of acetone under argon over night. Solvent was decanted from the oily residue which had formed. The oil was then washed twice with 2 mL of acetone and then triturated with another 10 mL of acetone to produce a powdery white solid. Solid dioxetane 3 was collected by suction filtration and washed with another 20 mL of acetone.

In an alternative procedure, the dioxetane product of step (d) can be directly converted to dioxetane 3 by by the following process. A solution of 2 mL of anhydrous pyridine and 10 mL of CH$_2$Cl$_2$ under argon is cooled to 0° C. and a solution of 0.424 g of POCl$_3$ in 10 mL of CH$_2$Cl$_2$ is added dropwise. After 15 min, a solution of 0.424 g of the dioxetane in 10 mL of CH$_2$Cl$_2$ is added dropwise. The solution is allowed to warm to room temperature and stirred for 4 h. The phosphate salt is formed and the ester groups are hydrolyzed by reacting the resulting dichlorophosphate dioxetane with 47.2 mg of NaOH in 1 mL of type I water and 10 mL of acetone under argon over night. The solvent is removed from the residue containing the product. The product is then washed with acetone and, if needed, triturated with acetone to produce a powdery white solid. Dioxetane 3 is collected by suction filtration.

Example 7
Discovery of Reagent Carryover Problem in Capsule Chemistry Analysis System The experiments described below were performed on a prototype capsule chemistry analysis system essentially as described by Kumar et al in U.S. Pat. No. 5,399,497, with the detection system configured to measure light emission (luminescence). The method and apparatus comprises feeding a stream of fluid segments through a Teflon tube, where the tube has an isolating layer of fluorocarbon oil on the inner surface. Sample and reagents are aspirated into this tube, and the resulting liquid segments are moved through the tube. Separation steps and washing steps which are required by heterogeneous immunoassay methods were facilitated by means of magnets, which transferred magnetic particles from one aqueous segment to another. The detection system was comprised of a photon counter and a fiber optic read head, in which the fibers were radially arranged around the Teflon tube to maximize the efficiency of light collection.

The TECHNICON IMMUNO 1® TSH method (Bayer Corporation, Tarrytown, N.Y., USA) was used as a representative immunoassay method for the testing of luminogenic reagents. The method principle involved incubation of a specimen containing the antigen TSH with a first reagent (R1), which contained a fluorescein-labeled antibody, and simultaneously with a second reagent (R2), which contained an antibody-alkaline phosphatase (ALP) conjugate. Each antibody was specific for a different epitope on the TSH antigen, so that formation of a "sandwich" was promoted between these two antibodies and the TSH antigen. Magnetic particles containing bound anti-fluorescein were used to capture the sandwich, and the particles were subsequently washed to remove unbound reagents. The particles were then exposed to the luminogenic reagent, which contained a substrate for ALP, and luminescence was measured.

The luminogenic R3 reagent was comprised of 0.2 mM CSPD (disodium 3-(4-methoxyspiro{1,2-dioxetane-3,2'-(5'-chloro)tricyclo [3.3.1.1$^{3,7}$]decan}-4-yl)phenyl phosphate, (Tropix, Inc., Bedford, Mass., USA), 3 mM pyranine (hydroxypyrenesulfonic acid), 1 mM MgCl$_2$, 1 M diethanolamine buffer (pH 10.0), 0.1% Triton X-100 and 0.1% NaN$_3$. The sequence of events on the capsule chemistry analysis system is depicted in FIG. 1 of the drawings. The fluid capsule or test package was comprised of six liquid segments, each of which had a volume of 28 µl. Magnetic particles (1.4 µl of the magnetic particle reagent used in the TECHNICON IMMUNO 1 system were aspirated into the first segment (MP), with the remainder of fluid being particle wash buffer (25 mM Tris, pH 7.5, containing 0.2 M NaCl, 0.1% Triton X-100 and preservative). R1 (10.4 µl of serum-based solution containing fluorescein-labeled antibody to TSH), R2 (10.4 µl of serum-based solution containing antibody to TSH conjugated with ALP) and S (7.2 µl of serum sample) were aspirated into the second segment. The next two segments (W1 and W2) were comprised of the same wash buffer used above in the MP segment. The fifth segment was R3, of the composition described above, with the key elements being the luminogenic substrate and the luminescence enhancer. The sixth segment was an inter-test buffer (same as the particle buffer described above), which was used to isolate adjacent tests. Magnetic transfers are depicted by the arrows in the FIG. 1. These transfers were facilitated by one of two magnetic transfer assemblies (M1 or M2). After an incubation of 13 minutes, during which sandwich formation occurred, M1 transferred the magnetic particles into the R1+R2+S segment to initiate capture.

After an additional period of 6 minutes, M2 transferred the particles into the first wash segment. After an additional period of 12 seconds, M2 transferred the particles into the second wash segment. After another period of 12 seconds, M2 transferred the particles into the R3 segment, and light emission from this segment was detected as the stream of aqueous segments passed back and forth through the luminometer readhead.

Figure 2:
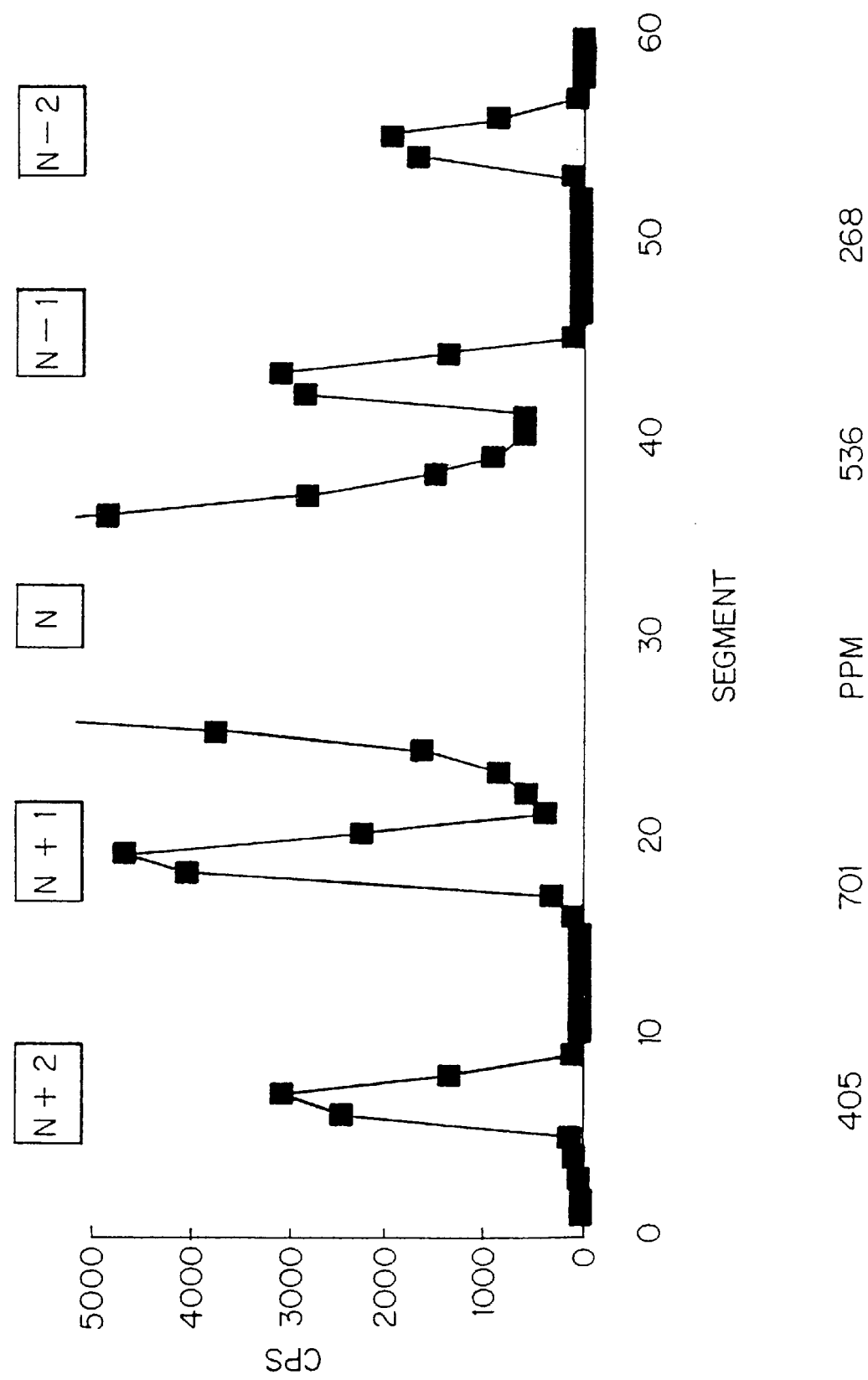
FIG. 2 is a profile of adjacent segments in the capsule chemistry analysis system showing the observed luminescence attributed to carryover as more fully described in the Examples below.

Since the Teflon tube is transparent to light, a problem with light piping (or "optical carryover") was expected. Specifically, some of the photons emitted from the R3 segment of an adjacent test could enter the Teflon material, propagate down the length of the tube and be scattered into the detector during the measurement of the signal of the test of interest. However, while a signal was detected in the adjacent tests, it did not occur in the expected manner. Instead of declining rapidly with distance from test N, peaks of light output were observed centered around the R3 segments of the adjacent test packages, as shown in FIG. 2 of the drawings. In FIG. 2, test N produced a high level of luminescence, approximately 7.5 million counts per seconds (cps). Tests N−1 and N−2 were aspirated into the tube before test N and preceded this test through the luminometer, and tests N+1 and N+2 followed after test N. The analysis system recorded photons counted for each individual air and liquid segment in the stream. The profile in FIG. 2 represents the average of 10 replicate panels of 5 tests each corrected for background luminescence signal produced in the absence of ALP. The reagent blank values subtracted from each data point were an average obtained from 10 replicate panels of 5 tests each. The magnitude of the carryover signal was computed by dividing the peak cps in each adjacent test by the peak cps in test N, expressed in parts per million (ppm).

Another possible explanation for this behavior was physical carryover of ALP from test N into the neighboring tests in an unintended manner. This could happen, for example, if the tube contained particulate materials deposited on the walls, which could disrupt the smooth motion of the liquid segments through the tube. However, placement of 10 mM inorganic phosphate in the R3 segments of the adjacent tests had no effect on the magnitude of the signals in the adjacent tests. Since this amount of phosphate would have inhibited ALP by at least 90% under these test conditions, the possibility of physical carryover was ruled out.

Figure 3:
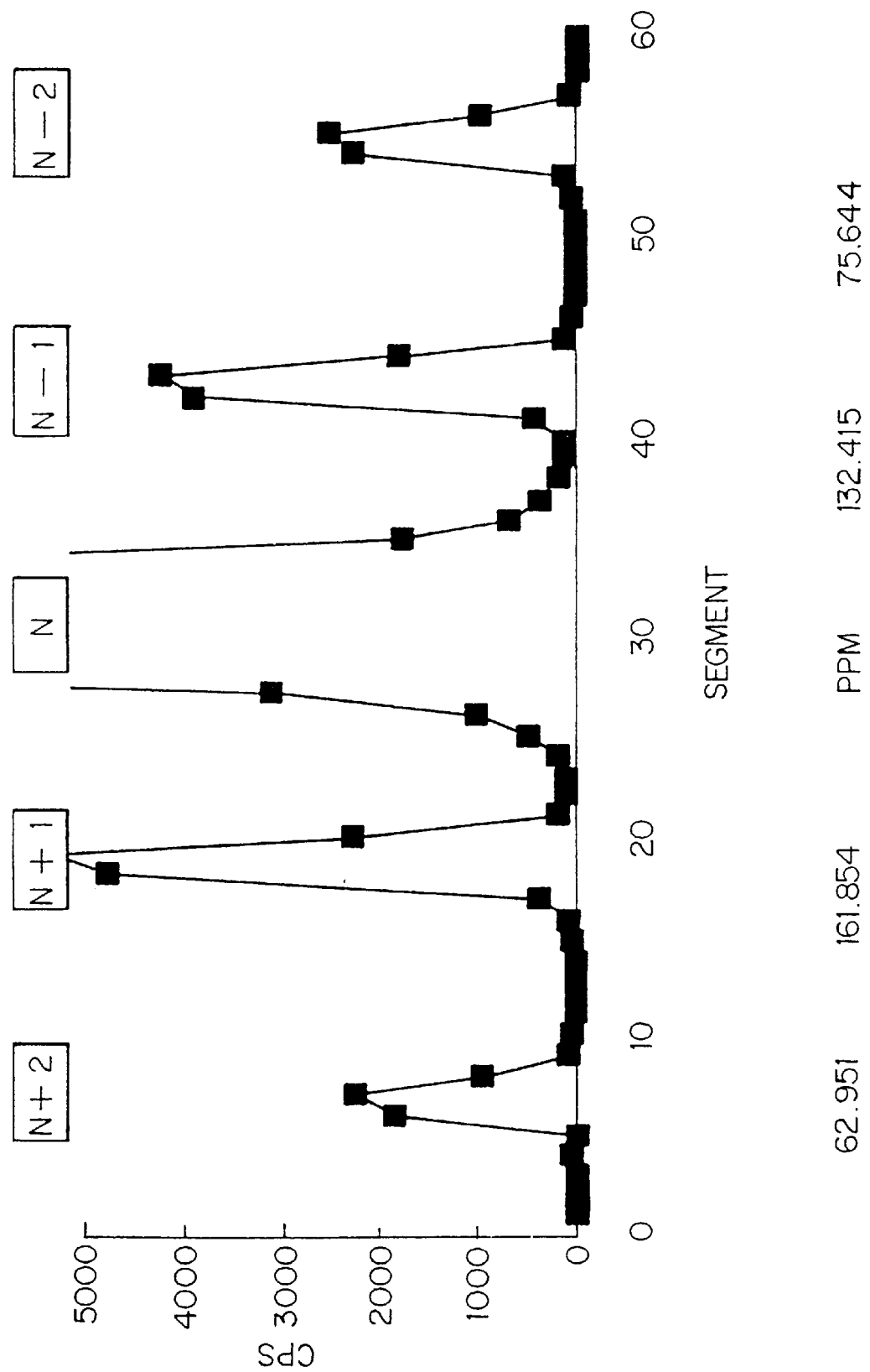
FIG. 3 is a further profile of adjacent segments observed in the experiments which are more fully described in the Examples below and which established that the carryover was not optical in nature.

To further rule out optical carryover, the fluorescent enhancer pyranine was omitted from test N only, but present in the adjacent tests. As a result, the magnitude of the signal in test N was lower by a factor of approximately 10. However, as shown in FIG. 3 of the drawings, the height of the peaks in the adjacent tests did not change significantly. The fact that the carryover signal did not change in the adjacent tests proportionately clearly demonstrated that this carryover was not optical.

Figure 4:
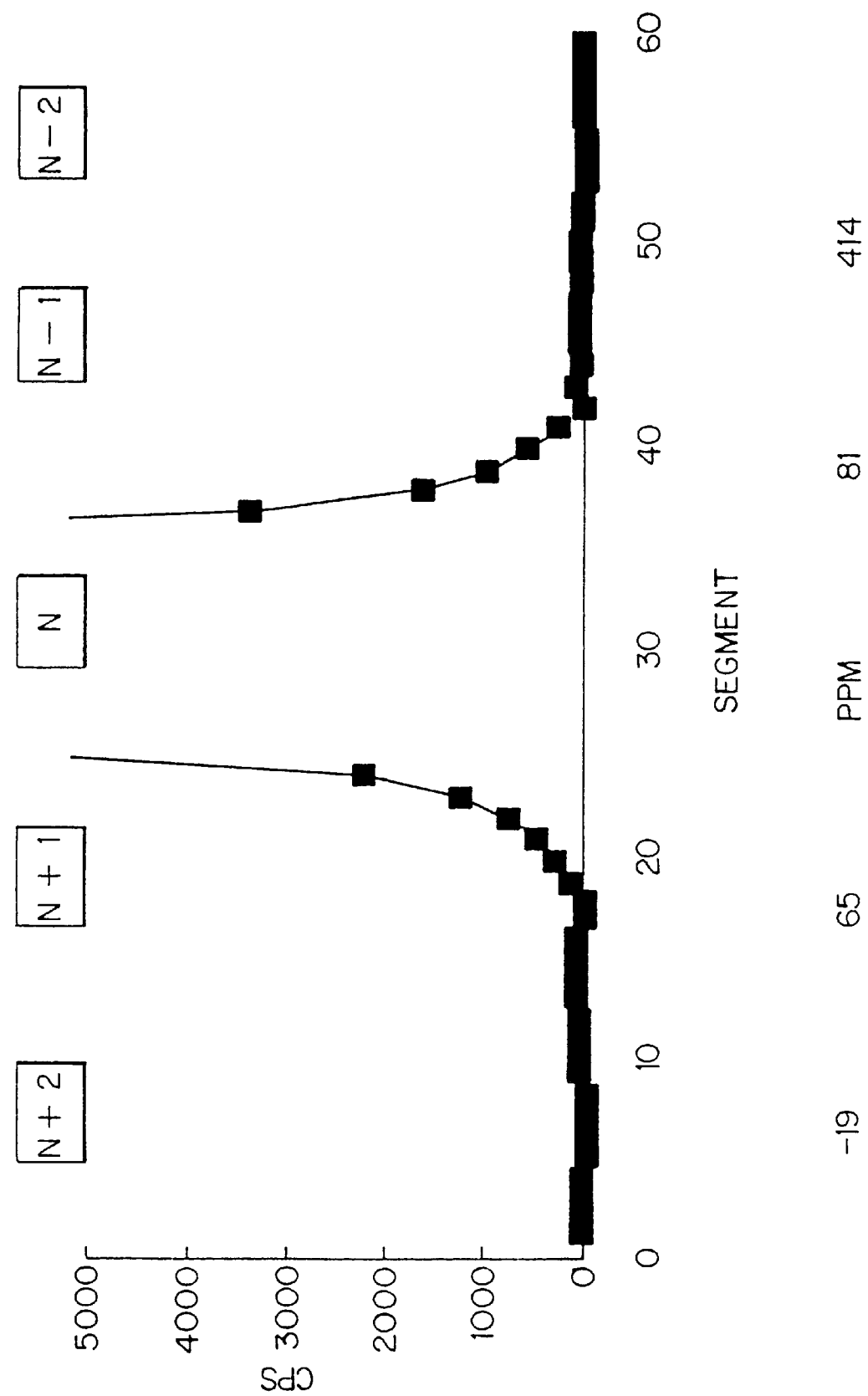
FIG. 4 is a further profile of adjacent segments observed in the experiments which are more fully described in the Examples below and which established that the carryover was in fact chemical in nature.

An additional and unexpected type of carryover was the cause of the carryover problem. It was found that the hydroxy dioxetane intermediate was sufficiently soluble in the fluorocarbon oil used to coat the inner wall of the Teflon tube, such that the carryover was due to transfer of dissolved hydroxy dioxetane intermediate via the oil into the R3 segments of the neighboring tests. This process was tested by changing the buffer of the R3 segments in the adjacent tests from 1 M DEA at pH 10 to 1 M Tris at pH 7. At pH 7, dissolved hydroxy dioxetane intermediate in these R3 segments is stable and does not emit light. As shown in FIG. 4 of the drawings, this change in pH resulted in the complete elimination of the side bands of luminescence. The residual minor carryover in the N+1 and N−1 tests was due to the anticipated optical carryover. These results verified that the source of light emission in the peaks in the neighboring tests was "chemical carryover" of the hydroxy dioxetane derived from CSPD into the R3 segments of adjacent tests.

Example 8

Elimination of Observed Chemical Carryover with Dicarboxylic Acid-Substituted Dioxetane 1

Table 1 shows the effect of using three other dioxetanes on the chemical carryover of the reaction intermediate. LUMIGEN PPD [4-(methoxy)-4-(3-phosphoryloxyphenyl)]spiro [1,2-dioxetane-3,2'-tricyclo[3.3.1.1$^{3,7}$]-decane], (Lumigen, Inc., Southfield, Mich., USA), dioxetane 2, a monocarboxylic acid derivative and dioxetane 1, a dicarboxylic acid derivative were each used in test formulations at the same concentration. The ppm column is the signal for the N+1 test, which represents worst case behavior. The carryover of the unmodified parent compound, PPD, was found to be more than twice as high as that observed with CSPD. Surprisingly, the monocarboxylic acid derivative, dioxetane 3, showed a reduction of only 84% in the magnitude of the chemical carryover. This indicated that a single charged group was insufficient to completely prevent solubilization of the reaction intermediate in the fluorocarbon oil. However, the dicarboxylic acid derivative was 100% effective, indicating that two charged groups were fully adequate to achieve the desired behavior.

TABLE 1

Reduction of Chemical Carryover

| Compound | ppm | % Reduction |
|---|---|---|
| LUMIGEN PPD | 1640 | |
| Dioxetane 2 | 260 | 84 |
| Dioxetane 1 | 0 | 100 |

Example 9

The Role of Enhancers

As part of the optimization of a reagent based on dioxetane 1, a number of enhancer materials was examined. At pH 9.6, Enhancer A (1-trioctylphosphoniummethyl-4-tributylphosphoniummethylbenzene dichloride) increased the luminescent signal by a factor of 6.2, and Enhancer B (poly(vinylbenzyltributylphosphonium chloride)) increased the signal by a factor of 19.7. At pH 10.0, Enhancer A increased the signal by a factor of 4.8, and Enhancer B increased the signal by a factor of 18.9.

Despite the fact that Enhancer B achieved higher light intensities, Enhancer A was preferred for use on the analysis system since it is a low molecular weight monomeric compound. Polymeric compounds, especially if they are polycationic, interact with serum components, causing precipitation, which would pose significant problems for the operation of the analysis system.

Both fluorescein and pyranine were found to be effective as supplementary fluorescers in combination with Enhancer A. Alone, these fluorescers must be used at relatively high concentrations (3 mM) in order to achieve an enhancement of about ten-fold. However, in combination with Enhancer A, a synergistic effect was observed, in which a comparable enhancement resulted at 100-fold lower concentrations of fluorescer than needed in the absence of the enhancer. Tables 2 and 3 show the extent of enhancement by pyranine and fluorescein, respectively, in the presence of 1 mg/mL of Enhancer A.

TABLE 2

Enhancement by Pyranine with Enhancer A

| [Pyranine] (mM) | Enhancement Factor |
|---|---|
| 0.01 | 3.7 |
| 0.02 | 7.3 |
| 0.03 | 9.8 |
| 0.04 | 12.2 |
| 0.05 | 13.7 |

TABLE 3

Enhancement by Fluorescein with Enhancer A

| [Fluorescein] (mM) | Enhancement Factor |
|---|---|
| 0.01 | 2.6 |
| 0.02 | 4.0 |
| 0.05 | 7.1 |
| 0.10 | 8.7 |

Example 10

Optimized Formulation for Capsule Chemistry Analysis System

The above described observations have led to the development of an optimized formulation for the capsule chemistry analysis system. This formulation is comprised of 0.1–1 mM dioxetane 1, 0–0.05 mM pyranine, 0.1–5 mg/mL Enhancer A, 0–1 mM $Mg^{+2}$, 0.1–1 M 2-amino-2-methyl-1-propanol (pH 10.0) and 0.01–1% Triton X-100. Use of this formulation results in complete elimination of the chemical carryover problem and enhanced performance.

Example 11

Stability of 1, 3, 4 and 5 Measured by Enzyme Assay.

Figure 5:
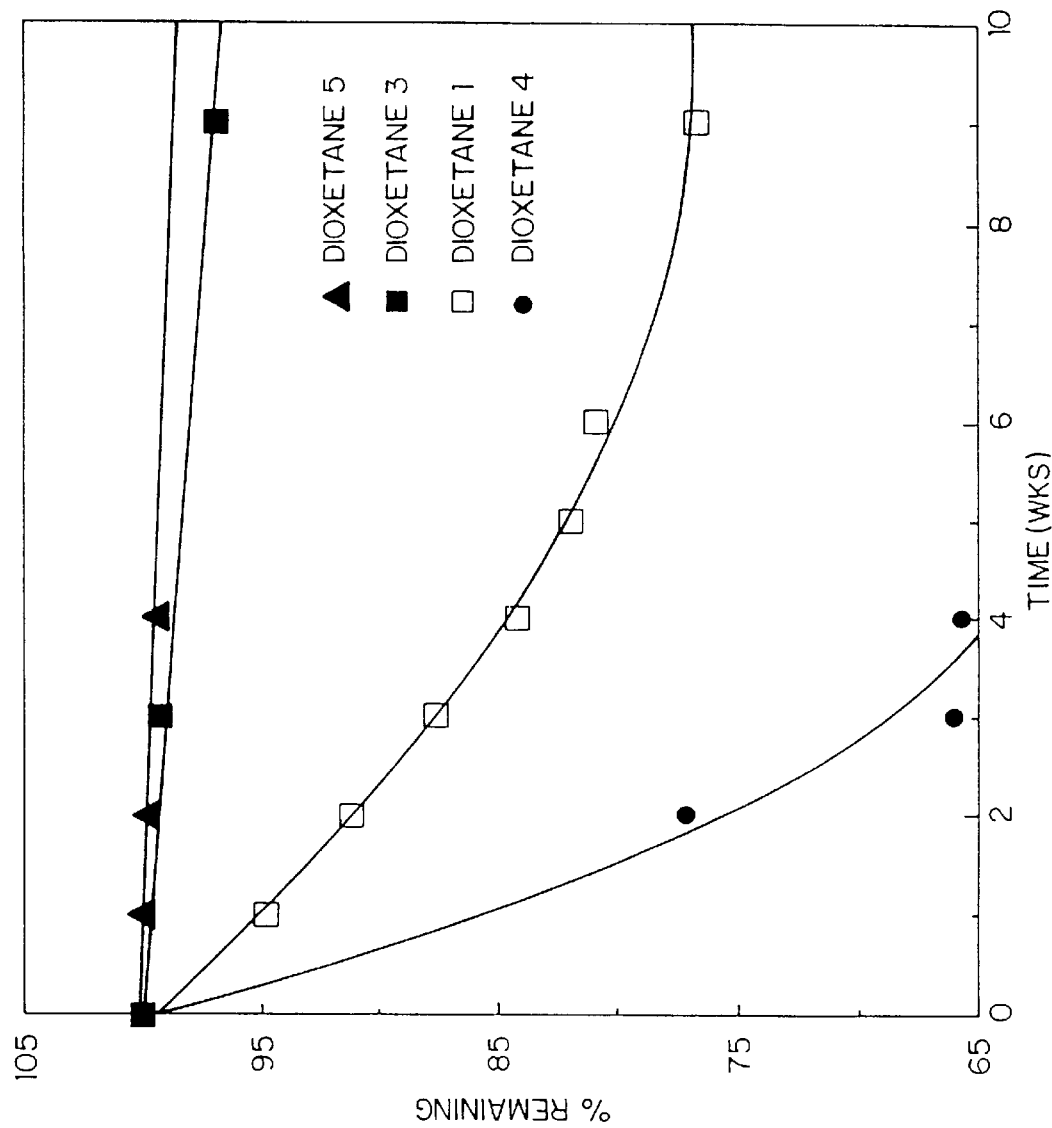
FIG. 5 is a graph depicting the relative rates of decomposition at 25° C. of a fluoro-substituted dioxetane, a chloro-substituted dioxetane, a methyl-substituted dioxetane and a reference dioxetane containing no halogen atoms.

Formulations comprising 0.1 mg/mL Enhancer A, 0.88 mM $Mg^{+2}$, 0.2 M 2-amino-2-methyl-1-propanol, pH 10, 0.1% Triton X-100 and 0.5 mM dioxetane 1, 3, 4 and 5, respectively, were prepared and stored in opaque polyethylene bottles at 4° C., 25° C. and 40° C. Twenty four 100 μL aliquots from each bottle were pipetted into the wells of a 96 well plate and the solutions incubated at 37° C. Into each well 10 μL solutions containing $8 \times 10^{-17}$ moles of AP were injected and light intensity integrated over five hours. Data are the average of all 24 wells. The experiment was repeated at the indicated time intervals for each dioxetane. The results in FIG. 5 show the comparative stability of the three formulations at 25° C. As shown in FIG. 5, fluoro-substituted dioxetane 3 was found to exhibit substantially better storage stability than chloro-substituted dioxetane 4 and non-halo-substituted dioxetane 1. Dioxetanes 3 and 5 were also substantially more stable than 1 or 4 at 40° C.

TABLE 4

Storage Stability of Formulations

| | % of Dioxetane Remaining | | | |
|---|---|---|---|---|
| Time (wks) | 1 | 3 | 4 | 5 |
| 0 | 100 | 100 | 100 | 100 |
| 1 | 94.8 | | | 100 |
| 2 | 91.1 | | 77.0 | 99.8 |
| 3 | 87.5 | 99.1 | 66.0 | |
| 4 | 84.1 | | 65.6 | 99.4 |
| 5 | 81.8 | | | |
| 6 | 80.7 | | | |
| 9 | 76.5 | 96.9 | | |
| 10 | | | 57.5 | |
| 12 | | 96.7 | | |
| 14 | | 93.8 | | |
| 21 | | 93.6 | | |

Example 12

Performance of 3

A detection reagent incorporating dioxetane 3 was evaluated in a test system as described in Example 7. The test material was a fluorescein-labeled alkaline phosphatase conjugate which was captured onto the magnetic particles. Assays for AP using the reagent containing 3 produced results with sensitivity, dynamic range and precision comparable to the results using dioxetane 1.

The foregoing examples are illustrative only and not intended to be restrictive. The scope of the invention is indicated only by the appended Claims and equivalents.

What is claimed is:

1. An alkene compound of the formula:

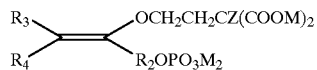

wherein $R_3$ and $R_4$ are each selected from the group consisting of acyclic, cyclic and polycyclic organic groups which can optionally be substituted with heteroatom substituents attached to the cyclic group and which can optionally be joined together to form a cyclic or polycyclic ring group, wherein $R_2$ is an aryl ring group selected from the group consisting of substituted or unsubstituted phenyl and substituted or unsubstituted naphthyl groups, wherein Z is selected from the group consisting of halogen atoms and alkyl groups of 1–4 carbons, and M is selected from hydrogen, an alkali metal ion or a quaternary ammonium or phosphonium ion.

2. The alkene of claim 1 wherein Z is selected from halogen atoms and alkyl groups of 1–4 carbons and each M is Na.

3. The compound of claim 2 wherein Z is F.

4. The compound of claim 2 wherein Z is $CH_3$.

5. An alkene compound of the formula:

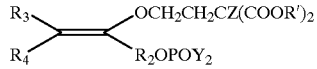

wherein $R_3$ and $R_4$ are each selected from the group consisting of acyclic, cyclic and polycyclic organic groups which can optionally be substituted with heteroatom substituents attached to the cyclic group and which can optionally be joined together to form a cyclic or polycyclic ring group, wherein $R_2$ is an aryl ring group selected from the group consisting of substituted or unsubstituted phenyl and substituted or unsubstituted naphthyl groups, wherein Z is selected from the group consisting of halogen atoms and alkyl groups of 1–4 carbons, wherein each R' is an alkyl group of 1–4 carbons and each Y is selected from halogen atoms, substituted or unsubstituted alkoxy, aryloxy, aralkyloxy and trialkylsilyloxy groups.

6. The compound of claim 5 wherein Z is F and each Y is a substituted alkoxy group.

7. The compound of claim 6 wherein each Y is a 2-cyanoethoxy group.

8. The compound of claim 5 wherein Z is $CH_3$ and each Y is a substituted alkoxy group.

9. The compound of claim 8 wherein each Y is a 2-cyanoethoxy group.

10. The compound of claim 5 wherein Z is F and each Y is a chlorine atom.

11. The compound of claim 5 wherein Z is $CH_3$ and each Y is a chlorine atom.

* * * * *